(12) United States Patent
Ueda

(10) Patent No.: US 7,278,969 B2
(45) Date of Patent: Oct. 9, 2007

(54) ULTRASONIC OBSERVATION SYSTEM

(75) Inventor: Masaaki Ueda, Sagamihara (JP)

(73) Assignee: Olympus Corporation, Tokyo (JP)

( * ) Notice: Subject to any disclaimer, the term of this patent is extended or adjusted under 35 U.S.C. 154(b) by 80 days.

(21) Appl. No.: 10/393,723

(22) Filed: Mar. 21, 2003

(65) Prior Publication Data

US 2004/0087854 A1 May 6, 2004

(30) Foreign Application Priority Data

| Mar. 25, 2002 | (JP) | ............................. 2002-084386 |
| Aug. 21, 2002 | (JP) | ............................. 2002-240933 |
| Mar. 13, 2003 | (JP) | ............................. 2003-068453 |

(51) Int. Cl.
*A61B 8/00* (2006.01)
*A61B 1/00* (2006.01)

(52) U.S. Cl. ...................... 600/463; 600/102

(58) Field of Classification Search ........ 600/444–446, 600/462–471, 102, 104, 106, 107, 114, 127, 600/129; 128/916

See application file for complete search history.

(56) References Cited

U.S. PATENT DOCUMENTS

| 4,858,613 | A | * | 8/1989 | Fry et al. ..................... 600/439 |
| 5,170,790 | A | * | 12/1992 | Lacoste et al. ............. 600/437 |
| 5,255,681 | A | * | 10/1993 | Ishimura et al. ............ 600/437 |
| 5,474,071 | A | * | 12/1995 | Chapelon et al. ........... 600/439 |
| 5,682,895 | A | * | 11/1997 | Ishiguro ..................... 600/440 |
| 5,820,559 | A | * | 10/1998 | Ng et al. ..................... 600/439 |
| 6,080,108 | A | * | 6/2000 | Dunham ..................... 600/459 |
| 6,106,472 | A |   | 8/2000 | Chiang et al. |
| 6,866,635 | B2 | * | 3/2005 | Flesch et al. ............... 600/459 |
| 2001/0027313 | A1 |   | 10/2001 | Shimmura et al. |
| 2003/0045768 | A1 |   | 3/2003 | Hirooka et al. |

FOREIGN PATENT DOCUMENTS

| JP | 6-261900 | 9/1994 |
| JP | 11-206764 | 8/1999 |

* cited by examiner

*Primary Examiner*—Francis J. Jaworski
(74) *Attorney, Agent, or Firm*—Scully, Scott, Murphy & Presser, P.C.

(57) ABSTRACT

An ultrasonic observation system of the invention includes a long ultrasonic probe having an ultrasonic sending and receiving portion, which can send and receive ultrasonic, and a holding portion, as a rotation operating portion, which can rotate the ultrasonic probe around an axis, which represents an arbitrary direction of oscillation directions of ultrasonic oscillated from the ultrasonic sending and receiving portion. A grasping portion is integrated with the holding portion. A contact portion is provided at the distal end of the grasping portion 613 and has an ultrasonic vibrator inside. A fixing frame is mounted to a distal end 622 of a holding unit 621 through a bearing 625 freely rotatably around a center axis S1 of the ultrasonic probe.

7 Claims, 18 Drawing Sheets

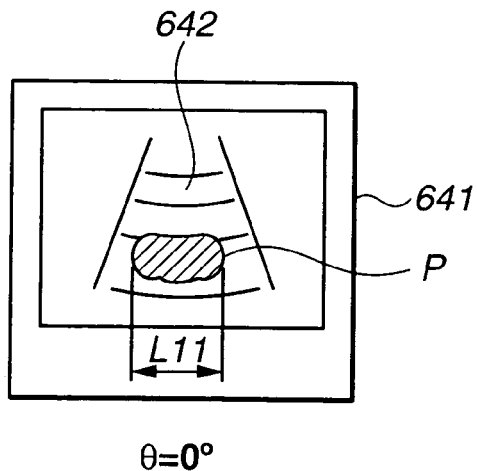
FIG.3  θ=0°
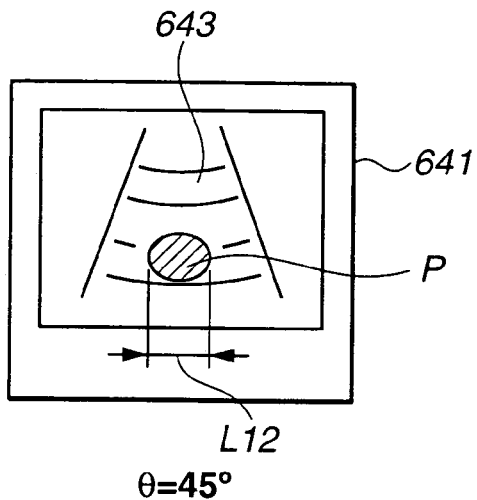
FIG.4  θ=45°
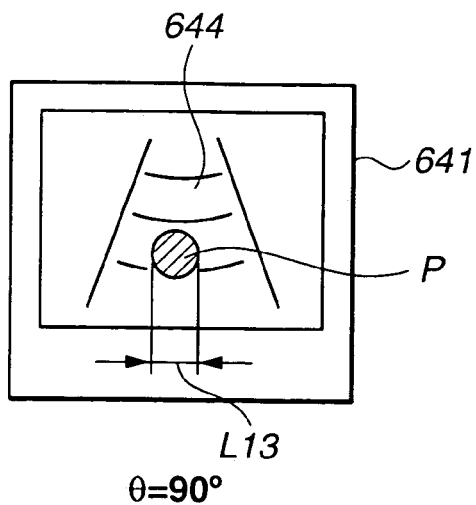
FIG.5  θ=90°

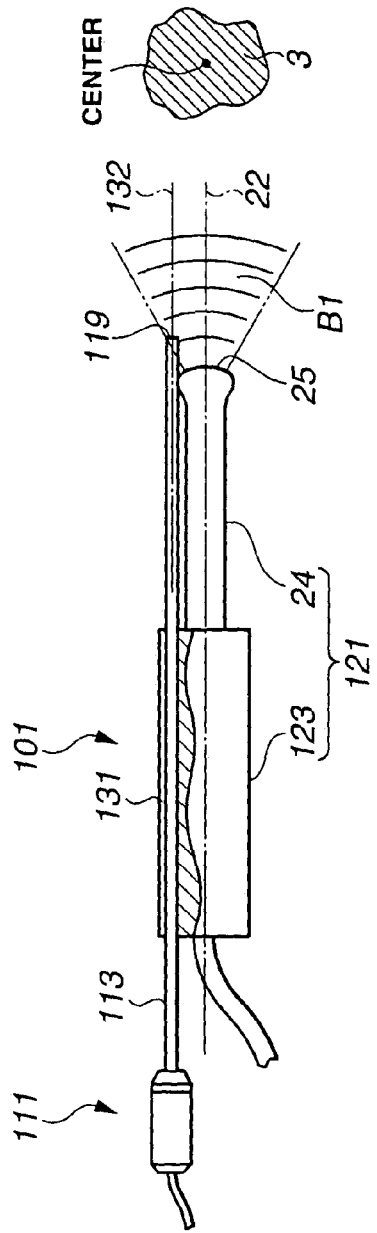
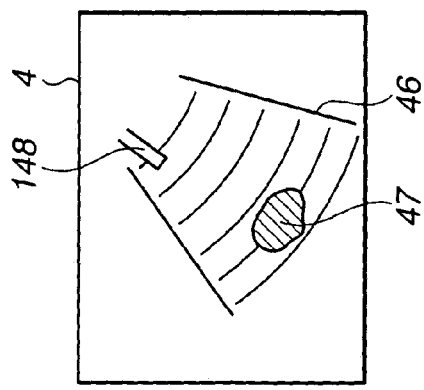
FIG.24
FIG.25

PRIOR ART

ULTRASONIC OBSERVATION SYSTEM

This application claims benefit of Japanese Application Nos. 2002-084386, filed in Japan on Mar. 25, 2002, 2002-240933, filed in Japan on Aug. 21, 2002, 2003-68453, filed in Japan on Mar. 13, 2003, the contents of which are incorporated by this reference.

BACKGROUND OF THE INVENTION

1. Field of the Invention

The present invention-relates to an ultrasonic observation system for ultrasonically observing an affected part in front of a part to be operated and, in particular, to an ultrasonic observation system used for extracting three-dimensional ultrasonic images in neurosurgery, for example.

2. Related Art Statement

Conventionally, in order to remove a tumor in a less invasive manner in neurosurgery, an endoscope has been often used.

In such a system, a treating apparatus is inserted to a treated part in the cranium while an operator watching an endoscope observation image in order to perform a treatment such as tumor removal. In this case, the endoscope is fixed and/or is supported by a medical equipment holding apparatus including multiple arms and joints. In the cranium, important tissue such as nerves and blood vessels are tangled complexly and minutely. Therefore, the holding apparatus needs to be able to move an endoscope minutely and smoothly so as not to hurt tissue and needs to be able to fix an endoscope at an accurate position.

A medical equipment holding apparatus disclosed in U.S. Pat. No. 2001/0,027,313A1 has been proposed as a system for holding and fixing an endoscope in order to perform such an operation.

In the medical equipment holding apparatus disclosed in U.S. Pat. No. 2001/0,027,313A1, an installing part is attached freely slidably at a side rail of an operating table. The installing part includes a link mechanism, which is a holding portion tilting mechanism, through a supporting arm, an upper supporting member, and a first parallel link mechanism. The holding portion in the link mechanism holds a rigid endoscope. With this construction, the first parallel link mechanism and the holding portion tilting mechanism arm are deformed without changing the position for installing the holding apparatus so as to change the direction of the rigid endoscope.

In the method for guiding a rigid endoscope toward a part to be operated, a part of the cranium is opened, and the treatment is then performed thereon blindly. In order to prevent this and to guide the rigid endoscope toward the part to be operated more securely, an in-operation X-ray observation apparatus or an in-operation ultrasonic observation apparatus is used as a measure for observing the distal end of the rigid endoscope in real time.

In general, when an ultrasonic observation apparatus is used, a part of the cranium is opened, and an ultrasonic probe incorporating an ultrasonic vibrator is then put on the surface of the brain so as to observe a part of the brain.

Such an ultrasonic observation apparatus is disclosed in U.S. Pat. No. 2003/0,045,768A1 and Unexamined Patent Application Publication No. 11-206764.

U.S. Pat. No. 2003/0,045,768A1 discloses an ultrasonic probe, which can be inserted to a part of a small opening. As shown in FIGS. 19 and 20, the sides and front of the inserting axis of the ultrasonic probe can be observed.

Unexamined Patent Application Publication No. 11-206764 discloses a so-called electronic scan type ultrasonic probe, which can observe the front part. According to the technology disclosed in the publication, the distal end of the ultrasonic probe is put on the surface of a living body such that an image several centimeters ahead from the surface of the living body can be observed.

In the ultrasonic observation, an operator observes a two-dimensional tomographic image (depth image) during an operation. Therefore, an ultrasonic probe is moved freely with respect to the head, and the rigid endoscope is guided to a part to be operated by checking a desired observed part.

Here, a two-dimensional tomographic image is observed in general ultrasonic observation. However, a three-dimensional image is desirably used for the observation in order to realize the accurate position and size of a tumor, for example. Therefore, the operator puts an ultrasonic probe on the brain surface, that is a part to be operated, during an operation and then moves the direction and/or position of the ultrasonic probe slightly. Thus, the operator observes two-dimensional images of the various conditions and then understands the various conditions as a three-dimensional image in his/her brain.

Unlike the conventional example in which an operator images a three-dimensional image from two-dimensional images in his/her brain as disclosed in Unexamined Patent Application Publication No. 11-206764, a conventional example in which a three-dimensional image can be obtained more easily has been proposed as disclosed in Unexamined Patent Application Publication No. 6-261900.

In an ultrasonic diagnosis apparatus disclosed in Unexamined Patent Application Publication No. 6-261900, at least one of a magnetic field generating means and a detecting means is positioned at the distal end of the ultrasonic probe, and a three-dimensional image forming means recognizes the relative position coordinates of the distal end or ultrasonic vibrator of the ultrasonic probe for the magnetic field generated by the magnetic field generating means based on a value detected by the detecting means. Then, the ultrasonic diagnosis apparatus forms a three-dimensional image by using a tomographic image of the ultrasonic probe and the recognized position coordinates while the operator is inserting and is retracting the ultrasonic probe by hand.

The three-dimensional-like state of the distal end of the endoscope may be required to recognize by using an ultrasonic probe for guiding the endoscope distal end as an observing unit to a part to be operated. In this case, according to the conventional technology, the distal end of an endoscope can be guided to a part to be operated securely by checking the movement continuously from the time immediately after the distal end is inserted to the head of a patient until the distal end reaches a part to be operated. In order to do so, the direction of a two-dimensional image imaged ultrasonically must substantially coincide with the plane including an inserting axis of the endoscope.

When an ultrasonic observation apparatus disclosed in U.S. Pat. No. 2003/0,045,768A1 and Unexamined Patent Application Publication No. 11-206764 is used in the cranial nerve field, the cranium is opened, and the ultrasonic probe must be put on the brain surface in order to obtain an image. In this case, from the operator's experience, the position of the ultrasonic probe is determined and is fixed, and then an endoscope is inserted thereto.

FIG. 30 is an explanatory diagram showing a positional relationship between the conventional endoscope and the ultrasonic probe.

As shown in FIG. 30, when a plane A0 including an inserting axis 502 of an endoscope 501 and a center axis 512 of an ultrasonic probe 511 is displaced from a two-dimensional plane (ultrasonic observation plane) B0 of an ultrasonic image rendered by the ultrasonic probe 511 by an angle α0, an endoscope distal end 503 does not appear on the ultrasonic image until the endoscope distal end 503 approaches the part to be operated.

On the other hand, in some operations, an ultrasonic probe may be inserted from an endoscope inserting hole, and the endoscope may be guided to a part to be operated while an operator checking the image information of the front of the endoscope. In this case, the operator inserts the ultrasonic probe as shown in U.S. Pat. No. 2003/0,045,768A1 and the endoscope alternately from the opening of the patient's head so as to access the part to be operated.

OBJECT AND SUMMARY OF THE INVENTION

Briefly, an ultrasonic observation system of the invention has a long ultrasonic probe having an ultrasonic sending and receiving portion, which can send and receive ultrasound, and a rotation operating portion, which can rotate the ultrasonic probe around an axis, which is an arbitrary direction of oscillation directions of ultrasound oscillated from the ultrasonic sending and receiving portion.

These object and advantages of the present invention will become further apparent from the following detailed explanation.

BRIEF DESCRIPTION OF THE DRAWINGS

FIG. 3 is an explanatory diagram showing a first display state of an ultrasonic image on a monitor according to the first embodiment of the invention;

FIG. 4 is an explanatory diagram showing the second display state of an ultrasonic image on a monitor according to the first embodiment of the invention;

FIG. 5 is an explanatory diagram showing a third display state of an ultrasonic image on the monitor according to the first embodiment of the invention;

FIG. 24 is a partial cut-out sectional view showing the ultrasonic probe according to the seventh embodiment of the invention;

FIG. 25 is an explanatory diagram of an ultrasonic image rendered by the ultrasonic probe according to the seventh embodiment of the invention;

DETAILED DESCRIPTION OF THE PREFERRED EMBODIMENTS

Embodiments of the invention will be explained below with reference to drawings.

First Embodiment

Figure 1:
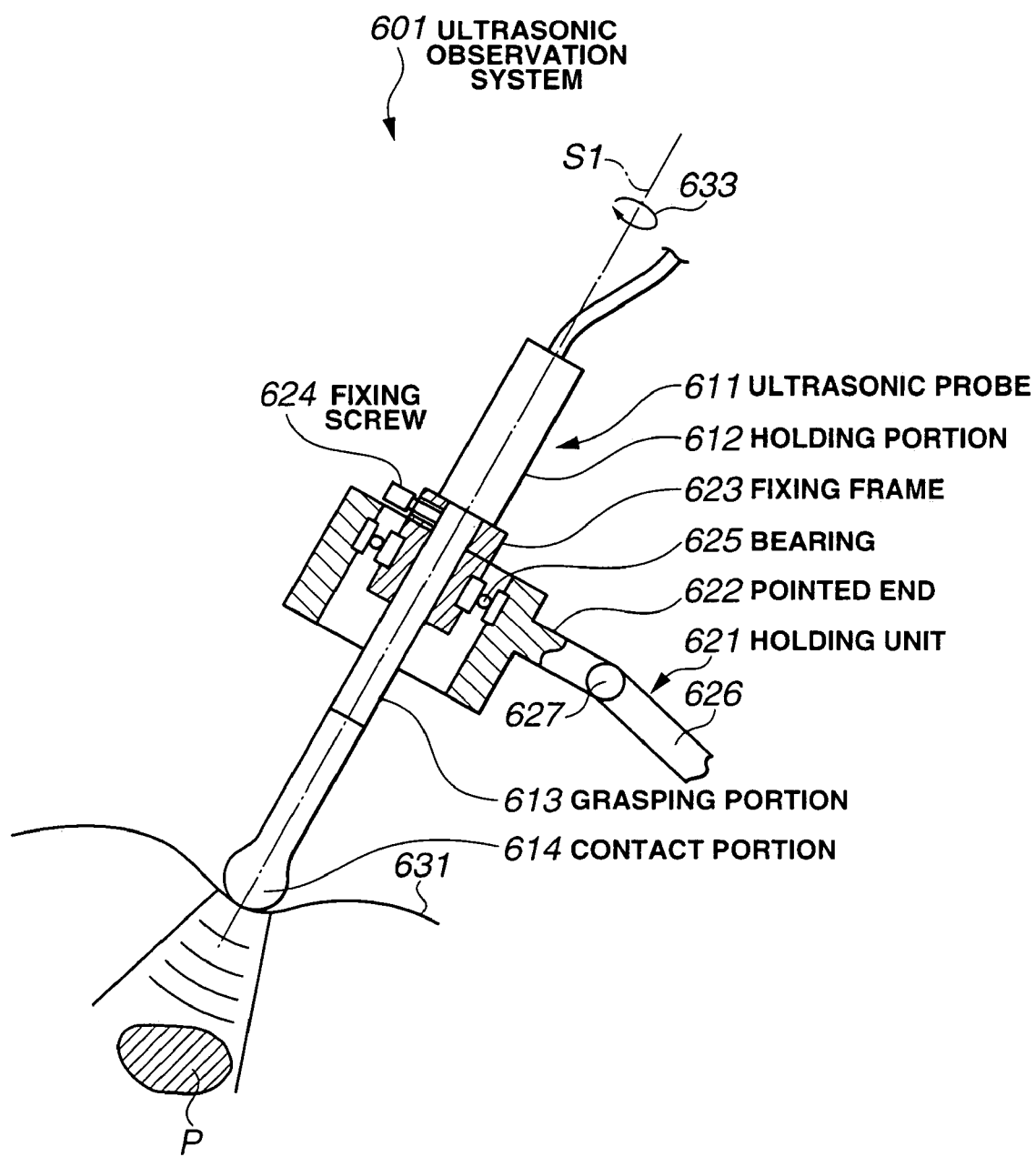
FIG. 1 is a configuration diagram showing an essential part of an ultrasonic observation system according to a first embodiment of the invention.
Figure 2:
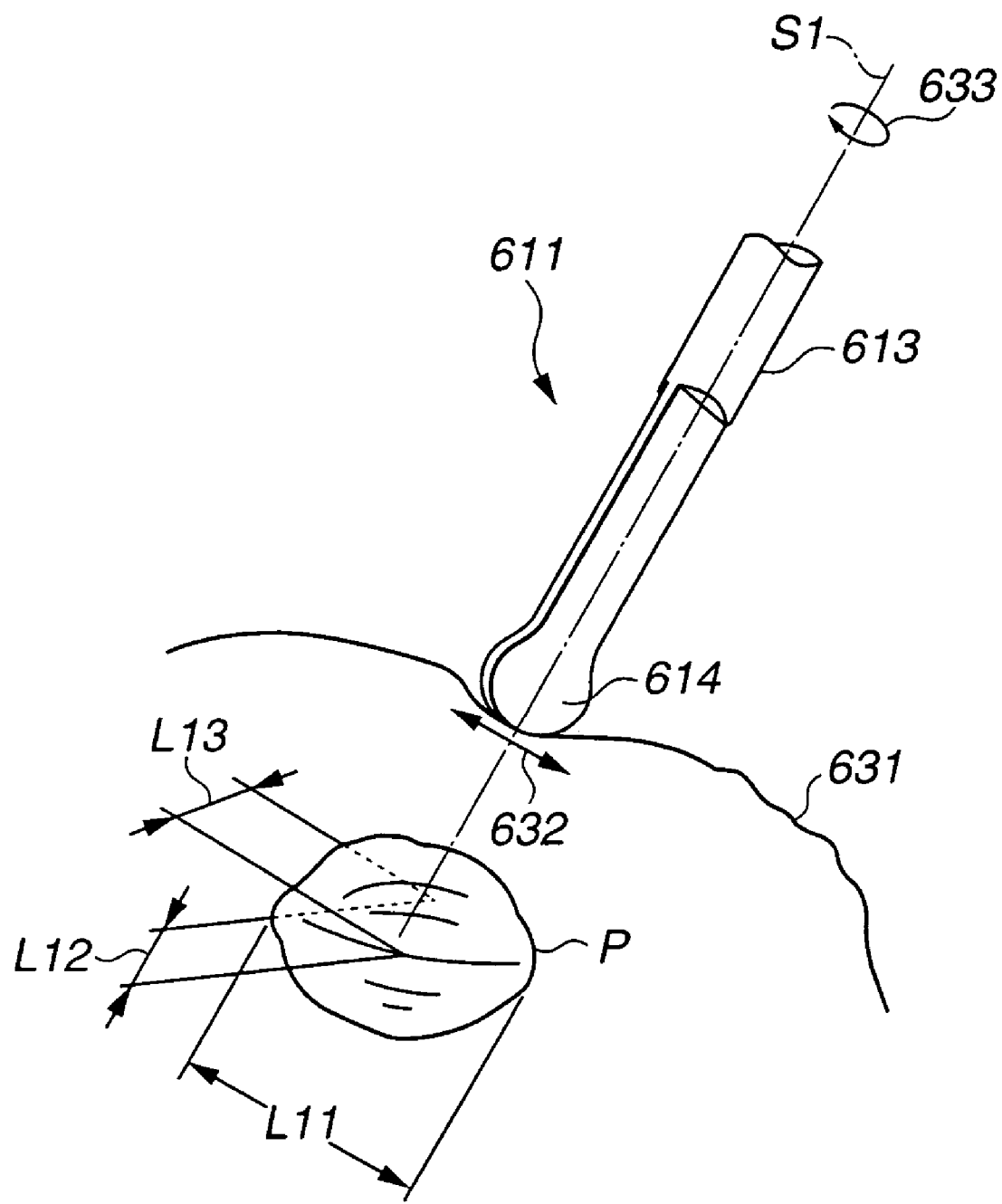
FIG. 2 is an explanatory diagram showing a scanning state of an affected part by an ultrasonic probe according to the first embodiment of the invention.

FIGS. 1 to 5 relate to a first embodiment. FIG. 1 is a configuration diagram showing an essential part of an ultrasonic observation system for ultrasonically observing an affected part by using an ultrasonic probe. FIG. 2 is an explanatory diagram showing a scanning state of an affected part by an ultrasonic probe. FIG. 3 is an explanatory diagram showing a first display state, on a monitor, of an ultrasonic image rendered by an ultrasonic probe. FIG. 4 is an explanatory diagram showing a second display state of an ultrasonic image on the monitor. FIG. 5 is an explanatory diagram showing a third display state of an ultrasonic image on the monitor.

[Construction]

In FIG. 1, an ultrasonic observation system 601 includes a long ultrasonic probe 611 having an ultrasonic sending and receiving portion, which can send and receive ultrasound, and a holding portion 612 as a rotation operating portion, which can rotate the ultrasonic probe around an axis which is in an arbitrary direction of oscillation directions of ultrasound oscillated from the ultrasonic sending and receiving portion.

A grasping portion 613 is integrated with the holding portion 612. A contact portion 614 is provided at the distal end of the grasping portion 613.

The contact portion 614 is the ultrasonic sending and receiving portion and has multiple ultrasonic vibrators in accordance with the form of the distal end of the contact portion 614 provided in consideration of the oscillated direction and operated direction of ultrasonic therewithin. In this case, the contact portion 614 can touch a surface 631 of the part to be operated and the internal ultrasonic vibrators send and receive ultrasonic to and from an affected part P.

A holding unit 621 holds the ultrasonic probe 611, and a distal end 622 on one end side has a fixing frame 623 associated with the grasping portion 613 of the ultrasonic probe 611.

The fixing frame 623 grasps and fixes the grasping portion, 613 integrally by using a fixing screw 624. A center axis S1 of the ultrasonic probe 611 indicates an arbitrary direction of directions for emitting ultrasonic from ultrasonic vibrators.

Furthermore, the fixing frame 623 is mounted freely rotatably at the distal end 622 of the holding unit 621 through a bearing 625 around the center axis S1 of the ultrasonic probe 611. In other words, the fixing frame 623, the bearing 625 and the distal end 622 form rotating means for allowing the ultrasonic probe 611 to rotate freely around the center axis S1.

The other end of the holding unit 621 is mounted at a frame in an operation bed, not shown, through a connecting portion. One end of the holding unit 621 is mounted at the distal end 622.

In other words, the holding unit 621 positions at a predetermined position the ultrasonic probe 611 rotatably grasped by the distal end 622, which is the rotating means, the fixing frame 623 and the bearing 625.

The holding unit 621 is moving means connected to the rotating means so as to allow the ultrasonic probe 611 to move three-dimensionally, wherein the holding unit 621 has multiple arms and further has multiple joints for physically coupling the multiple arms so as to move the distal end 622 three-dimensionally.

One arm 626 of the multiple arms is coupled (connected) with the distal end 622, through one joint 627 of the multiple joints. These joints have brakes for properly regulating the movement of the ultrasonic probe 611 and form movement regulating means.

The brake is preferably an electromagnetic brake, whose ON/OFF can be switched electrically. The ON/OFF switching of the electromagnetic brake is preferably a hand switch at a desired position of the multiple arms or a foot switch at operator's feet.

[Operation]

According to the first embodiment, an operator operates the holding unit 621 first for recognizing the size and/or form of an affected part P (such as a brain tumor) shown in FIG. 1 to make contact the contact portion 614 of the ultrasonic probe 611 with the surface 631 of the part to be operated when the direction of a length L11 of the affected part P coincides with a scanning direction 632, which is the same as the direction of the two-dimensional image plane obtained ultrasonically, as shown in FIG. 2. In this case, as shown in FIG. 3, a tomographic image of a two-dimensional plane in which the size of the affected part P is equal to L11 is displayed on an ultrasonic observation image 642 on a monitor 641.

Next, the operator grasps the holding unit 612 of the ultrasonic probe 611 by hand and rotates the ultrasonic probe 611 by an angle $\theta$ in a direction indicated by an arrow 633 around the center axis S1. In this case, the ultrasonic probe 611 is grasped by the holding unit 621 through the fixing frame 623 and the bearing 625. Therefore, the ultrasonic probe 611 is rotated without any displacement of the contact portion 614, that is, the center axis S1 three-dimensionally. For example, when $\theta=45°$, a scanning direction 632 of the ultrasonic probe 611 shown in FIG. 2 coincides with the length L12 of the affected part P. In this case, as shown in FIG. 4, a tomographic image of the two-dimensional plane in which the size of the affected part P is equal to L12 is displayed on an ultrasonic observation image 643 of the monitor 641.

Furthermore, when $\theta=90°$, the scanning direction 632 of the ultrasonic probe 611 shown in FIG. 2 coincides with the length L13 of the affected part P. In this case, as shown in FIG. 5, a tomographic image of the two-dimensional plane in which the size of the affected part P is equal to L13 is displayed on an ultrasonic observation image 644 on the monitor 641. Similarly, by rotating the ultrasonic probe 611 intermittently up to $\theta=360°$ around the center axis S1, a tomographic image of a two-dimensional plane including the scanning direction 632 at the angle $\theta$ is displayed on the monitor 641.

Thus, the operator observes and understands ultrasonic information (a tomographic image of a two-dimensional plane) of an object from $\theta=0°$ to $\theta=360°$, which is obtained by the ultrasonic probe in accordance with the rotation of the holding portion 612, as a three-dimensional image of the object in his/her brain. In other words, the operator can recognize the three-dimensional state of the object.

[Advantages]

According to the first embodiment, a three-dimensional state of an object to be observed in an operation space can be recognized. In other words, the state of the affected part can be recognized securely as the three-dimensional form and size with the simple construction in which a rotating means for allowing the rotation around the center axis S1 is provided at the distal end 622 of the holding unit 621 without any displacement of the position of the contact portion 614, which is the distal end of the ultrasonic probe 611.

Since the ultrasonic probe 611 can be always held by the holding unit 621 without any displacement, an ultrasonic observation image can be always observed even while an operator is treating the part to be operated. Therefore, more secure treatment becomes possible on an affected part.

Figure 31:
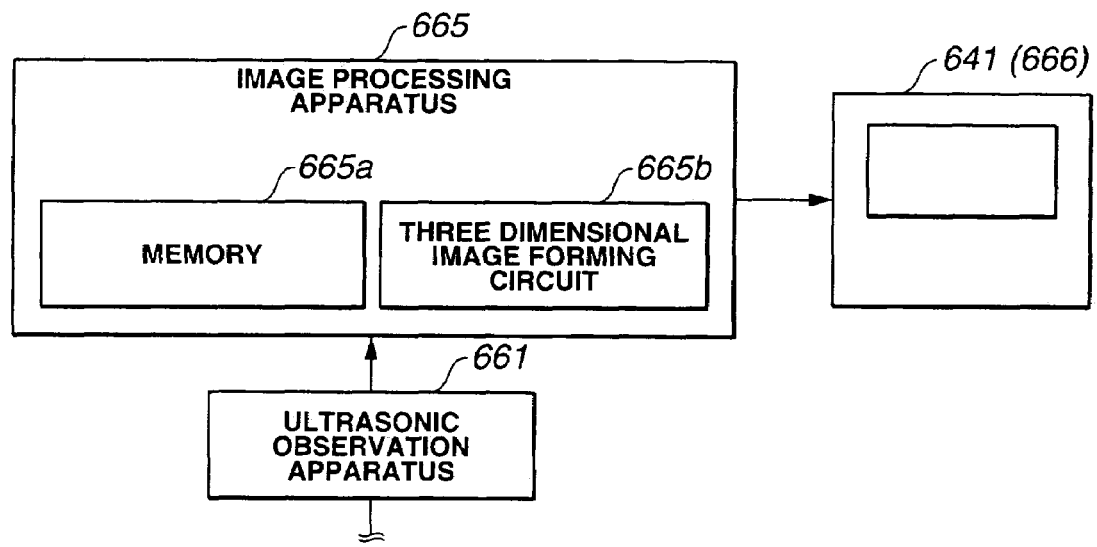
FIG. 31 is a block diagram showing a variation example of the first embodiment of the invention and showing additional circuits for creating a three-dimensional image.

Furthermore, according to the first embodiment, by further having the block construction shown in FIG. 31, a three-dimensional image of the object is formed with the simple construction such that the three-dimensional state of the object can be recognized.

More specifically, the ultrasonic probe 611 is electrically connected to an ultrasonic observation apparatus 661 shown in FIG. 31.

The ultrasonic observation apparatus 661 is electrically connected to an image processor 665. Thus, ultrasonic information on an object (such as two-dimensional image information and position information of the ultrasonic probe) obtained by the ultrasonic probe 611 in accordance with the rotation operation of the holding portion 612 is supplied to the image processor 665.

The position information of the ultrasonic probe 611 can be obtained with the construction shown in FIG. 6, which will be described later in detail. In other words, the position information of the ultrasonic probe 611 can be obtained by the ultrasonic probe 651 shown in FIG. 6, multiple light-emitting diodes 656 provided in the ultrasonic probe 651, a three-dimensional observation apparatus 662, which can measure the three-dimensional positions of the multiple light-emitting diodes 656, and a workstation 664, which can calculate position information of the ultrasonic probe 651 (611) based on change (variation) information of the positions of the multiple light-emitting diodes 656 measured by the three-dimensional observation apparatus. The position information of the ultrasonic probe 651 (611) is supplied from the workstation 664 to the image processor 665.

The image processor 665 performs processing for displaying an ultrasonic observation image of an object, which is obtained by the ultrasonic probe 611, in accordance with the rotation operation of the holding portion 612. The image processor 665 includes a memory 665*a* and a three-dimensional image forming circuit 665*b*.

The memory 665*a* stores position information of the ultrasonic probe 651 (611) from the workstation 664 and a two-dimensional ultrasonic observation image of an object, which is obtained by the ultrasonic probe 611 in accordance with the rotation operation of the holding portion 612.

The three-dimensional image forming circuit 665*b* performs processing on the position information and two-dimensional ultrasonic observation image from the memory 665*a* to perform processing for forming a three-dimensional image. Then, the three-dimensional image forming circuit 665*b* outputs the three-dimensional image to the monitor 641 (monitor shown in FIGS. 3 to 5).

In the ultrasonic observation system with the above-described construction, like the ultrasonic observation system shown in FIG. 1, an operator observes and understands ultrasonic information (a tomographic image of a two-dimensional plane) of an object ranged from $\theta=0°$ to $\theta=360°$, which is obtained by the ultrasonic probe 611 in accordance with the rotation operation of the holding portion 612, as a three-dimensional image of the object in his/her brain. By further providing the block construction shown in FIG. 31 thereto, the three-dimensional image of the object can be formed and be displayed on the monitor 641 based on the ultrasonic information (a tomographic image of a two-dimensional plane and position information) of an object ranged from $\theta=0°$ to $\theta=360°$, which is obtained by the ultrasonic probe 611 in accordance with the rotation operation of the holding portion 612.

In other words, in order to capture an object as a three-dimensional image by using a conventional ultrasonic probe, a two-dimensional image are shot in the direction for inserting and retracting to/from an object, and the two-dimensional images are aligned in order. Thus, a three-dimensional image is formed. That is, an image is obtained in which sliced images are stacked.

On the other hand, according to this embodiment, an ultrasonic probe can be rotated around the center axis S1, which is an arbitrary direction of directions for oscillating ultrasonic oscillated from the ultrasonic probe 611. Therefore, an object can be shot at various angles from one direction without relatively moving the ultrasonic probe 611 with respect to the object. Based on the obtained multiple two-dimensional images, a three-dimensional image can be formed around the axis in the arbitrary one direction by using the ultrasonic observation apparatus 661 and the image processor 665.

Thus, a part to which is difficult to insert a probe, such as the brain, can be ultrasonically observed by using three-dimensional images.

In other words, according to this embodiment, the three-dimensional state of an object to be observed in an operation space can be recognized. That is, the three-dimensional ultrasonic image can be rendered easily by using the ultrasonic observation system 601 for ultrasonically observing an affected part in front of the object to be operated in neurosurgery. Therefore, the affected part can be treated securely with the reduction of the burden on the operator.

Second Embodiment

Figure 6:
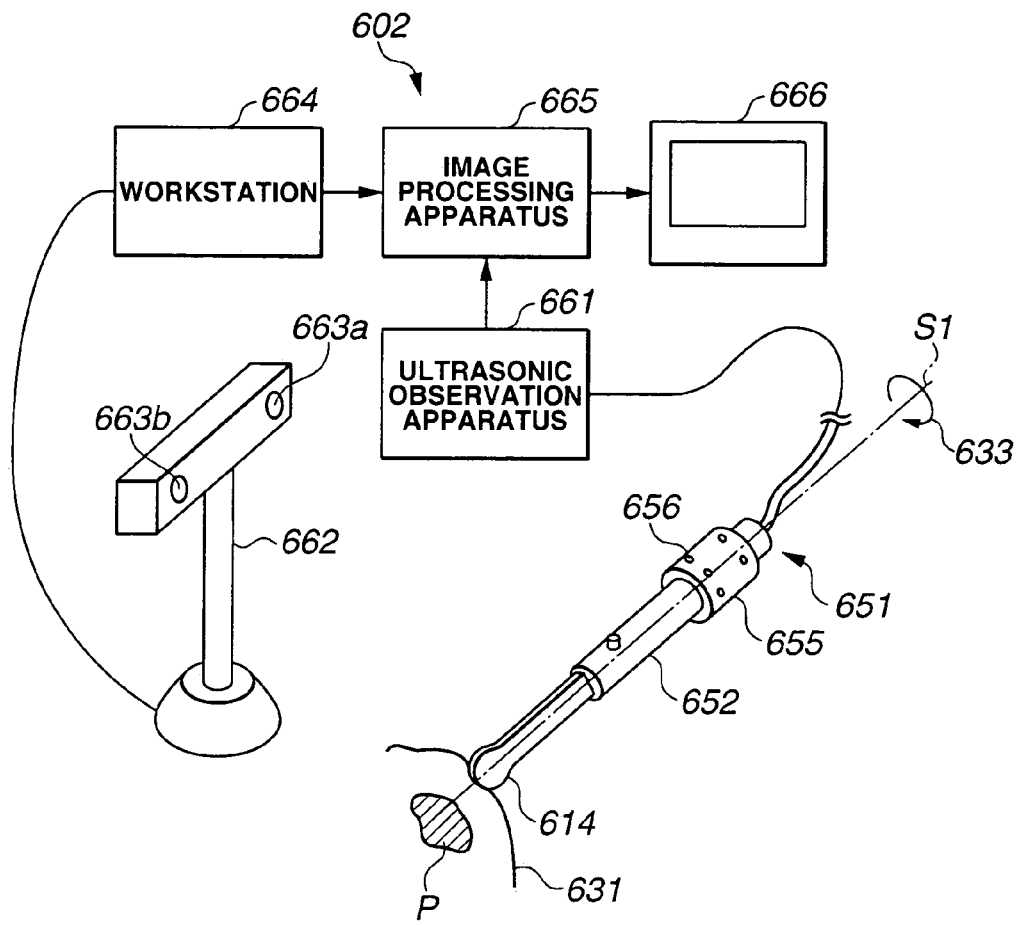
FIG. 6 is a configuration diagram showing an essential part of an ultrasonic observation system according to a second embodiment of the invention.
Figure 7:
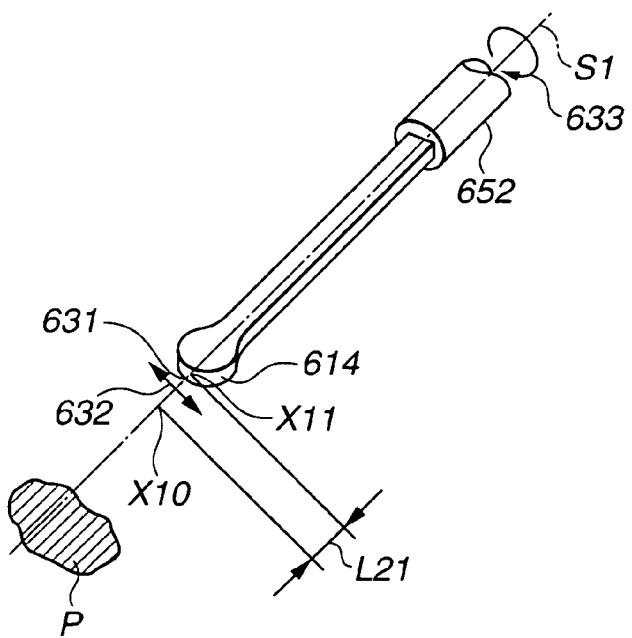
FIG. 7 is an explanatory diagram showing a scanning state of an affected part by an ultrasonic probe according to the second embodiment of the invention.
Figure 8:
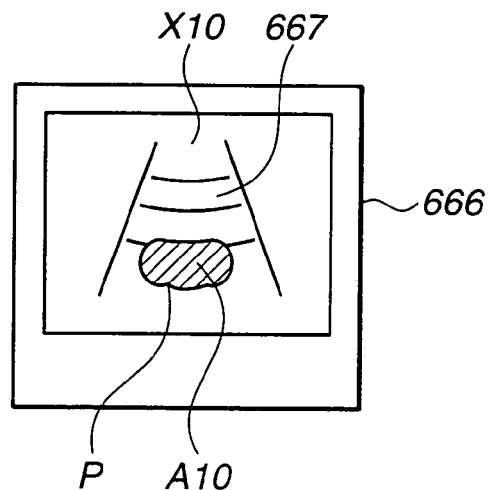
FIG. 8 is an explanatory diagram showing a first display state of an ultrasonic image on a monitor according to the second embodiment of the invention.
Figure 9:
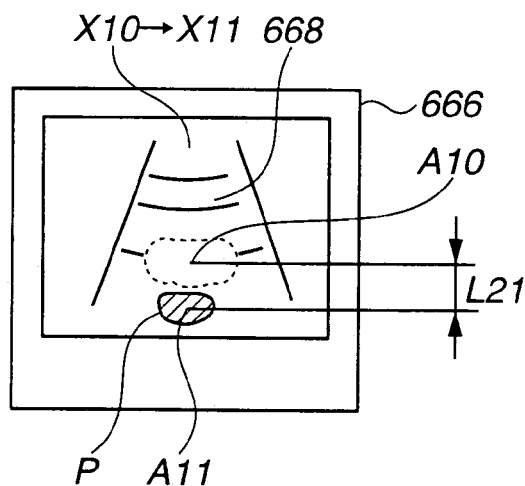
FIG. 9 is an explanatory diagram showing a second display state of an ultrasonic image on the monitor according to the second embodiment of the invention.
Figure 10:
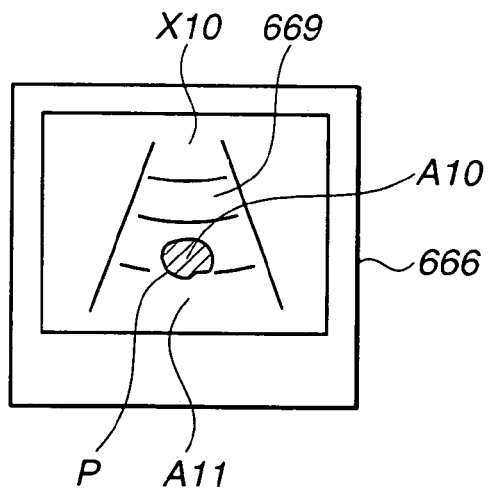
FIG. 10 is an explanatory diagram showing a third display state of an ultrasonic image on the monitor, which is rendered by an ultrasonic probe according to the second embodiment of the invention.

FIGS. 6 to 10 relate to a second embodiment of the invention. FIG. 6 is a configuration diagram showing an essential part of an ultrasonic observation system for ultrasonically observing an affected part by using an ultrasonic probe. FIG. 7 is an explanatory diagram showing a scanning state of an affected part by an ultrasonic probe. FIG. 8 is an explanatory diagram showing a first display state of an ultrasonic image on a monitor, which is rendered by the ultrasonic probe. FIG. 9 is an explanatory diagram showing a second display state of an ultrasonic image. FIG. 10 is an explanatory diagram showing a third display state of an ultrasonic image.

In the description of the second embodiment with reference to FIGS. 6 to 10, the same reference numerals are given to the same components as those of the first embodiment, and the description will be omitted here.

[Construction]

As shown in FIG. 6, an ultrasonic observation system 602 includes an ultrasonic probe 651, a sensor arm 655, an ultrasonic observation apparatus 661, a three-dimensional observation apparatus 662, a workstation 664, an image processor 665 and a monitor 666.

The ultrasonic probe 651 has a holding portion 652 as a rotation operating portion, which can rotate the ultrasonic probe 651 around a center axis S1.

A contact portion 614 is provided at the distal end of the holding portion 652 and has an ultrasonic vibrator inside.

The sensor arm 655 is mounted to the holding portion 652 of the ultrasonic probe 651. Multiple light-emitting diodes 656 are mounted on the periphery of the sensor arm 655.

The multiple light-emitting diodes 656 are signal generating portions at a predetermined positions (positions apart from the distal end of the contact portion 614 by a known distance) with respect to the contact portion 614, which is the ultrasonic sending and receiving portion. In other words, the multiple light-emitting diodes 656, which are signal generating portions, are located accurately in advance at positions apart from the center axis S1 and the distal end of the contact portion 614 by a know distance. Therefore, the direction of the center axis of the ultrasonic probe 651 and the position information indicating the distal end of the contact portion 614 can be detected by these light-emitting diodes 656, the three-dimensional observation apparatus 662, which will be described later, and the workstation 664.

Photoreceptive cameras 663a and 663b for receiving infrared rays emitted by the light-emitting diodes 656 are mounted to the three-dimensional apparatus 662. Thus, the three-dimensional observation apparatus 662 can be a receiving portion for receiving signals from the signal generating portions.

The three-dimensional observation apparatus 662 is connected to the workstation 664. The workstation 664 is a first three-dimensional-position calculating means, which can calculate the three-dimensional position and posture of the ultrasonic probe based on information on the signal generating portions obtained from the receiving portion, that is, change information (variation information) of positions of the multiple light-emitting diodes 656.

Thus, the sensor arm 655, the three-dimensional observation apparatus 662 and the work station 664 can be included in three-dimensional-position determining means, that is a so called navigation equipment, for determining the position of the contact portion 614, which is the distal end of the ultrasonic probe 651, with respect to an affected part P. U.S. patent application (application No. U.S. Pat. No. 2003/0,045,768) discloses such a known navigation equipment, and the contents of U.S. Pat. No. 2003/0,045,768 are incorporated by this reference.

The ultrasonic observation apparatus 661 and the workstation 664 are connected to the image processor 665.

Almost like the first embodiment (see FIG. 31), the image processor 665 performs processing for displaying ultrasonic observation images of an object to be operated, which is obtained from the ultrasonic observation by rotating the ultrasonic probe 651. The image processor 665 includes a memory 665a and a three-dimensional image forming circuit 665b.

The memory 665a stores ultrasonic information (two-dimensional ultrasonic observation images) obtained from the ultrasonic observation by rotating the ultrasonic probe 651 and probe position information obtained by the probe position detecting means (first three-dimensional position calculating unit).

The three-dimensional image forming circuit 665b performs processing on the probe position information and the two-dimensional ultrasonic observation images from the memory 665a to form and output a three-dimensional image to a monitor 666 (see FIG. 31).

The image processor.665 may be image display control means for correcting the displacement of the position displaying an ultrasonic observation image on the monitor 666 due to the displacement of the ultrasonic probe 651 with respect to an affected part P.

[Operation]

In the second embodiment, an operator holds the holding portion 652 of the ultrasonic probe 651 shown in FIG. 6 by hand, puts the contact portion 614 at the distal end on a surface 631 of the part to be operated and ultrasonically observes the affected part P.

Here, a tomographic image of the affected part P is displayed on an ultrasonic observation image 667 on the monitor 666, as shown in FIG. 8.

Next, like the first embodiment, the operator rotates the ultrasonic probe 651 in the direction indicated by the arrow 633 around the center axis S1. Here, since the operator holds the ultrasonic probe 651 by hand, the displacement of the contact portion 614 at the distal end, such as the displacement by a distance L21 from a point X10 to a point X11 as shown in FIG. 7, occurs with the rotation. The three-dimensional observation apparatus 662 receives infrared rays emitted by the light-emitting diodes 656 mounted to the sensor arm 655 through photoreceptive cameras 663a and 663b. Therefore, the three-dimensional observation apparatus 662 continuously detects the change in positions of the light-emitting diodes 656.

The displaced amount L21 can be calculated by the workstation 664 based on the amount of change in positions of the light-emitting diodes 656. In other words, since the light-emitting diodes 656 are positioned apart from the rotation axis S1 and the contact portion 614 by known distances, the displaced amount L21 of the contact portion 614 at the distal end of the ultrasonic probe 651 can be calculated. The displaced amount L21 is output to the image processor 665. Additionally, an ultrasonic observation image of the affected part P is output from the ultrasonic observation apparatus 661 to the image processor 665.

Conventionally, in this case, as shown in FIG. 9, a displacement (from A10 to A11, for example) of the displaced amount L21 of the displayed image occurs in the ultrasonic observation image 668 on the monitor 666 according to the displacement of the contact portion 614 at the distal end of the ultrasonic probe 651 on the surface 631 of the part to be operated.

However, in the second embodiment, the displaced amount L21 is corrected by the image processor 665, and, as shown in FIG. 10, a tomographic image of the affected part P is displaced accurately at the point A10 on the ultrasonic observation image 669 on the monitor 666. In other words, like the first embodiment, a tomographic image of the affected part P is displayed on the monitor 666 as the tomographic image of a two-dimensional plane including the scanning direction 632 in accordance with the rotation of the ultrasonic probe 651 without any displacement of the reference position of the affected part P on the monitor 666.

[Advantages]

According to the second embodiment, a three-dimensional state of an object to be observed in an operation space can be recognized. In other words, since the positional displacement due to the rotation of the ultrasonic probe 651 can be corrected in combination with the navigation equipment, an operator can use the ultrasonic probe 651 in a freehand manner without loss of the operability of the conventional ultrasonic probe 651.

Third Embodiment

Figure 11:
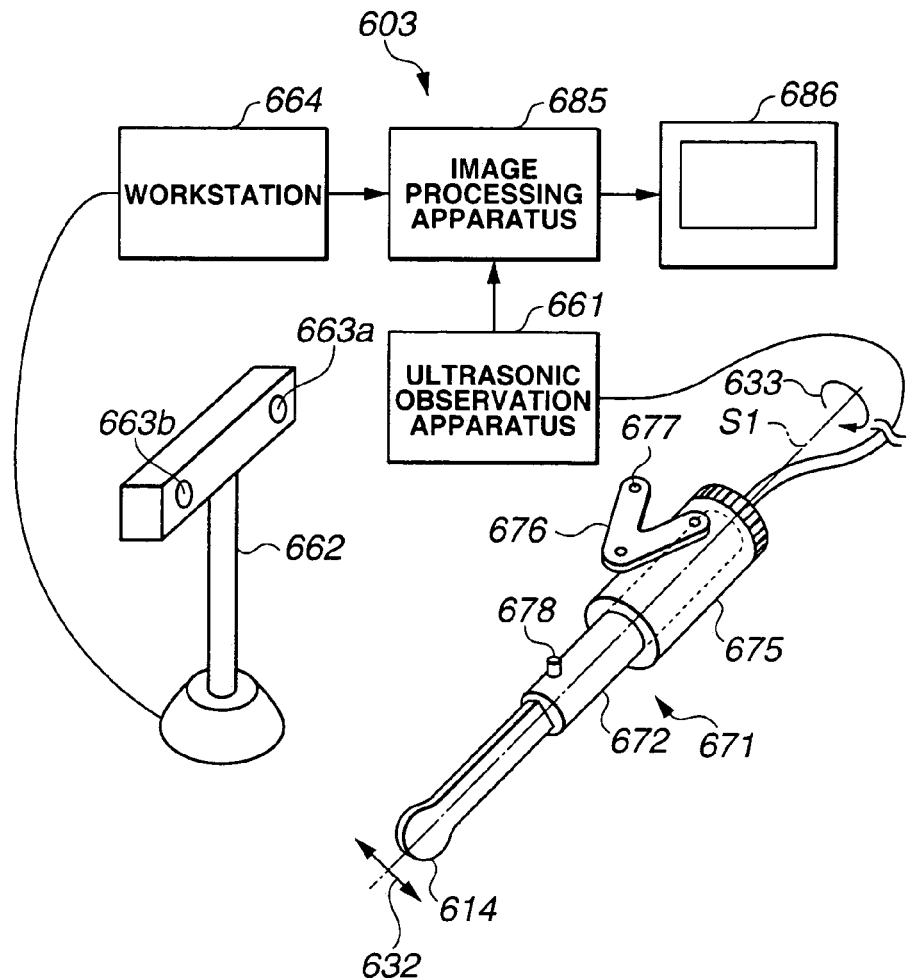
FIG. 11 is a configuration diagram showing an entire construction of an ultrasonic observation system according to a third embodiment of the invention.
Figure 12:
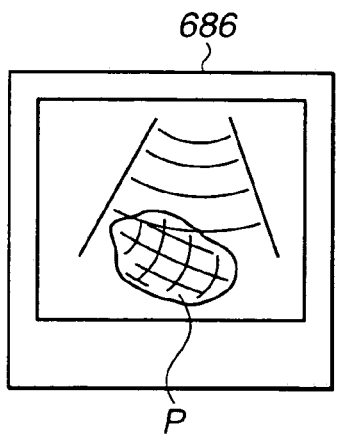
FIG. 12 is an explanatory diagram showing a display state of an ultrasonic image on a monitor according to the third embodiment of the invention.

FIGS. 11 and 12 relate to a third embodiment of the invention. FIG. 11 is a configuration diagram showing an entire construction of an ultrasonic observation system for ultrasonically observing an affected part by using an ultrasonic probe. FIG. 12 is an explanatory diagram showing a display state of an ultrasonic image.

In the description of the third embodiment with reference to FIGS. 11 and 12, the same reference numerals are given to the same components as those of the second embodiment, and the description will be omitted here.

[Construction]

An ultrasonic observation system 603 includes an ultrasonic probe 671, a pallium tube 675, an ultrasonic observation apparatus 661, a three-dimensional observation apparatus 662, a workstation 664, an image processor 685, and a monitor 686.

The pallium tube 675 freely rotatably holds the ultrasonic probe 671 inside around the center axis S1.

A sensor arm 676 is mounted at a part of the periphery of the pallium tube 675. At least three light-emitting diodes 677 are mounted in the sensor arm 676.

Like the second embodiment, these light-emitting diodes 677 are located at predetermined positions (positions apart from the distal end of the contact portion 614 by known distances) with respect to the contact portion 614, which is the ultrasonic sending and receiving portion and are positioned around the center axis S1. Thus, the axial direction of the ultrasonic probe 671 can be detected by using at least two of the light emitting diodes 677. By using three light-emitting diodes 677, the amount of rotation around the center axis S1 and three-dimensional position of the entire ultrasonic probe 671 can be detected.

An input switch 678 is provided in a holding portion 672 of the ultrasonic probe 671. The input switch 678 is used for inputting stored two-dimensional ultrasonic observation image data including the scanning direction 632 of the contact portion 614 to the image processor 685 through the ultrasonic observation apparatus 661. Alternatively, the input switch 678 may be provided at a position where the input switch 678 can be operated easily on the pallium tube 675 instead of on the holding portion 672.

Like the second embodiment, the workstation 664 is connected to the image processor 685. The workstation 664 is included in a navigation equipment for correcting displacement of an image due to the displacement of the ultrasonic probe 671.

Figure 32:
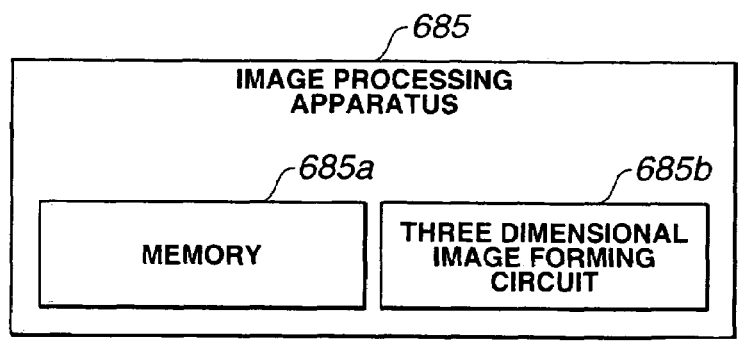
FIG. 32 is a block diagram showing a configuration example of an image processor shown in FIG. 11 according to the third embodiment of the invention.

Almost like the first embodiment, as shown in FIG. 32, the image processor 685 includes a memory 665a and a three-dimensional image forming circuit 685b. The memory 665a stores the two-dimensional ultrasonic observation image and the position information of an object, which are input from the ultrasonic observation apparatus 661. The three-dimensional image forming circuit 685b performs processing on the position information and two-dimensional ultrasonic observation image from the memory 665a to form a three-dimensional image.

A 3D monitor 686 is connected to the image processor 685 and displays images based on the output signals of the image processor 685.

[Operation]

In the third embodiment, an operator holds the pallium tube 675 of the ultrasonic probe 671 and makes the contact portion 614 contact with an object to be operated, like the second embodiment. Then, the operator rotates the holding portion 672 with respect to the pallium tube 675 by 360° in a direction indicated by an arrow 633 around the center axis S1.

In this case, like the second embodiment, the ultrasonic observation is performed in which the displacement of the contact portion 614 of the ultrasonic probe 671 is corrected by the navigation equipment including the sensor arm 676, the three-dimensional observation apparatus 662, and the workstation 664.

Furthermore, the operator presses the input switch 678 on the holding portion 672 of the ultrasonic probe 671. Thus, the two-dimensional ultrasonic observation image including the scanning direction 632 of the ultrasonic probe 671 is output from the ultrasonic observation apparatus 661 to the image processor 685. At the same time, the image processor 685 corrects the displaced amount of the image based on the correction information from the workstation 664 for the displacement of the probe distal end position and then stores the corrected image in the memory 685a (see FIG. 32). In the same manner, the operator presses the input switch 678 while the operator is rotating the ultrasonic probe 671 in the direction indicated by the arrow 633 around the center axis S1.

Thus, the two-dimensional ultrasonic observation image in accordance with the intermittent rotation about the center axis S1 of the ultrasonic probe 671 is stored in the memory 685a of the image processor 685.

Then, the operator rotates the ultrasonic probe 671 by 360°, and the two-dimensional ultrasonic observation images of the perimeter are stored in the memory 685a. Then, the operator presses a three-dimensional image forming switch (not shown) of the image processor 685. Then, the image processor 685 forms a three-dimensional ultrasonic observation image from the two-dimensional ultrasonic observation images stored in the memory 685a by using the three-dimensional image forming circuit 685b. Then, the image processor 685 outputs image signals to the 3D monitor 686.

Thus, the 3D monitor 686 displays the three-dimensional ultrasonic observation image of the affected part P as shown in FIG. 12.

[Advantages]

According to the third embodiment, a three-dimensional state of a part to be observed in an operation space can be recognized. In other words, since an affected part P is displayed as a three-dimensional image, the state of the affected part, such as the shape and size, can be recognized easily and securely.

The ultrasonic probe 671 includes the pallium tube 675 and the body, and the sensor arm 676 is mounted to the pallium tube 675 and the body of the ultrasonic probe 671 is made to be able to rotate with respect to the pallium tube 675. Thus, the ultrasonic probe 671 can be rotated more easily in the direction indicated by the arrow 633 around the center axis S1. As a result, the displaced amount of the contact portion 614 due to the rotation can be reduced. Furthermore, the precision of detection of the ultrasonic probe 671 by the navigation equipment can be improved, and more precise three-dimensional images can be formed.

Fourth Embodiment

Figure 13:
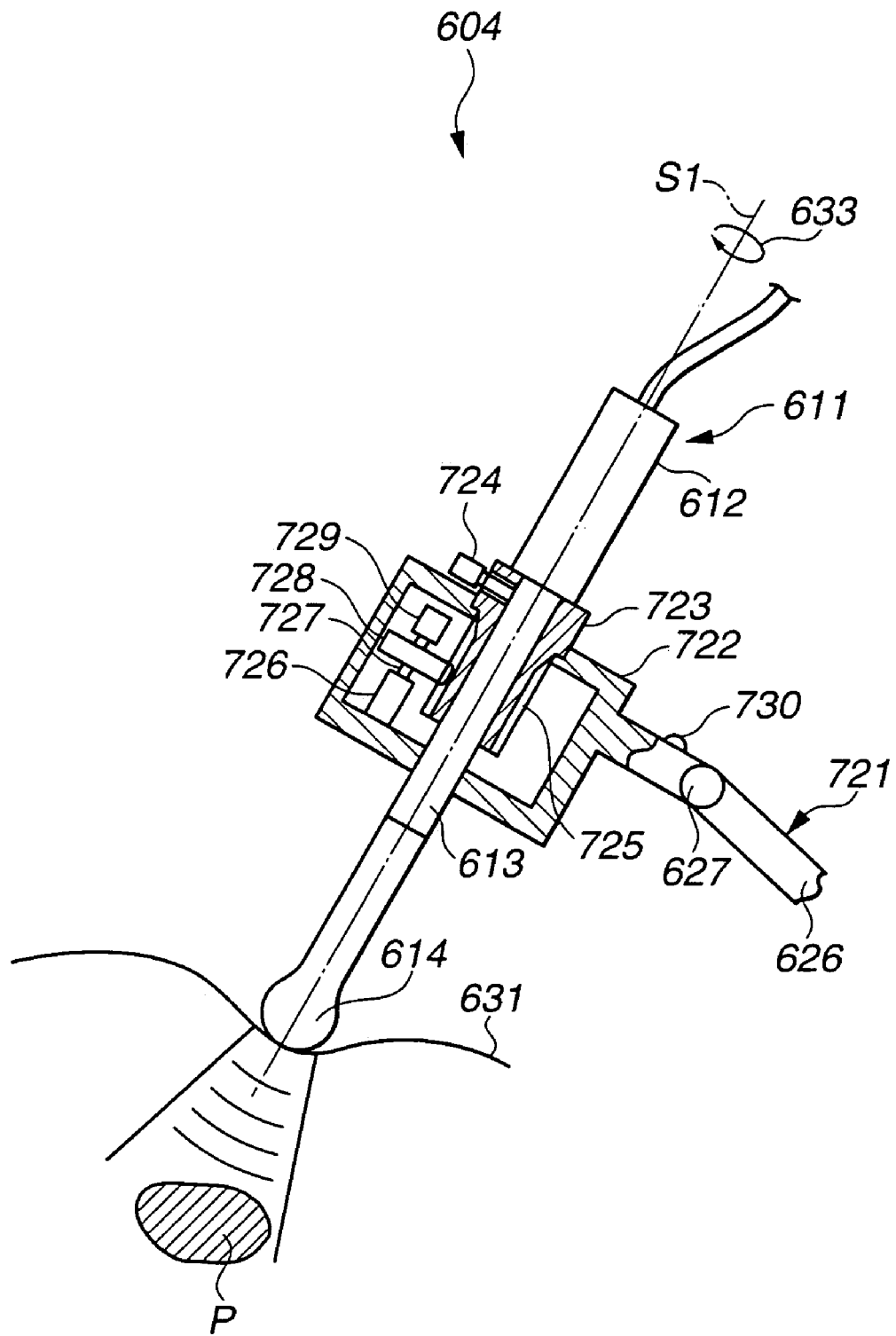
FIG. 13 is a configuration diagram showing an essential part of an ultrasonic observation system according to a fourth embodiment of the invention.

FIG. 13 is a configuration diagram showing an essential part of an ultrasonic observation system for ultrasonically observing an affected part by using an ultrasonic probe according to a fourth embodiment of the invention.

In the description for the fourth embodiment with respect to FIG. 13, the same reference numerals are given to the same components as those of the first embodiment, and the description will be omitted here.

[Construction]

In FIG. 13, an ultrasonic observation system 604 includes an ultrasonic probe 611 and a holding portion 612.

A holding unit 721 holds the ultrasonic probe 611.

Like the first embodiment, a distal end 722 of the holding unit 721 includes a fixing portion 723, a motor 726, a gear 728 and an encoder 729 inside. The fixing portion 723 holds and fixes a grasping portion 613 of the ultrasonic probe 611.

In this case, a fixing frame 723 grasps and fixes the grasping portion 613 integrally by using a fixing screw 724.

A gear 725 is provided on the periphery of the fixing portion 723. The motor 726 is provided and is fixed within the distal end 722. The gear 728 is mounted to an output axis 727 of the motor 726. The gear 728 is screwed to the gear 725 on the periphery of the fixing portion 723.

Furthermore, the encoder 729 is mounted to the output axis 727. The encoder 729 detects the rotational angle of the gear 728. For example, when the gear ratio of the gear 728 to the gear 725 is 1:1, the rotational angle of the gear 728 is the rotational angle in the direction indicated by the arrow 633 of the ultrasonic probe 611 around the center axis S1. An input switch 730 is provided at the distal end 722. The input switch 730 is used to drive the motor 726.

Thus, the input switch 730 is a rotation operating portion, which can rotate the ultrasonic probe 611 around the center axis S1.

[Operation]

In the fourth embodiment, like the first embodiment, an operator operates the holding unit 721 and puts the contact portion 614 of the ultrasonic probe 611 on a surface 631 of the part to be operated to perform ultrasonic observation on an affected part P. Then, the input switch 730 at the distal end 722 of the holding unit 721 is turned on. Thus, the motor 726 is driven, and the fixing portion 723 and the ultrasonic probe 611 are rotated through the gear 728 in the direction indicated by the arrow 633 around the center axis S1. Additionally, the rotational angle of the ultrasonic probe 611 is detected by the encoder 729. When the rotational angle of the ultrasonic probe 611, which is detected by the encoder 729, is in the range of 0° to 360°, two-dimensional ultrasonic observation images from the ultrasonic probe 611 are output to the image processor 685 through the ultrasonic observation apparatus 661 and are stored in the memory, like the third embodiment shown in FIG. 11.

Thus, like the third embodiment, a three-dimensional ultrasonic observation image is displayed on the 3-D monitor 686 shown in FIG. 12.

[Advantages]

According to the fourth embodiment, a three-dimensional state of an object to be observed in an operation spade can be recognized. In other words, a rotating mechanism is provided at the distal end of the holding unit 721 and can rotate by 360° without displacement with respect to the contact portion 614 at the distal end of the ultrasonic probe 611. Therefore, a three-dimensional image can be rendered more precisely.

Fifth Embodiment

Figure 14:
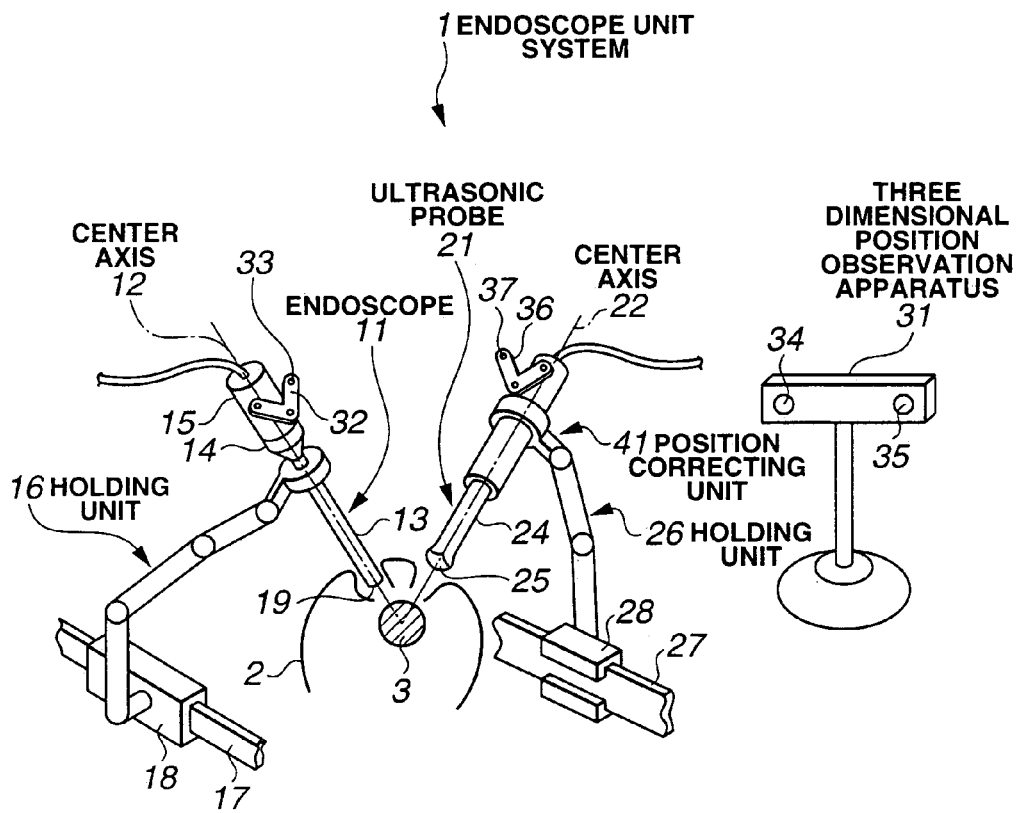
FIG. 14 is an explanatory diagram showing an entire construction of an endoscope operation system according to a fifth embodiment of the invention.
Figure 15:
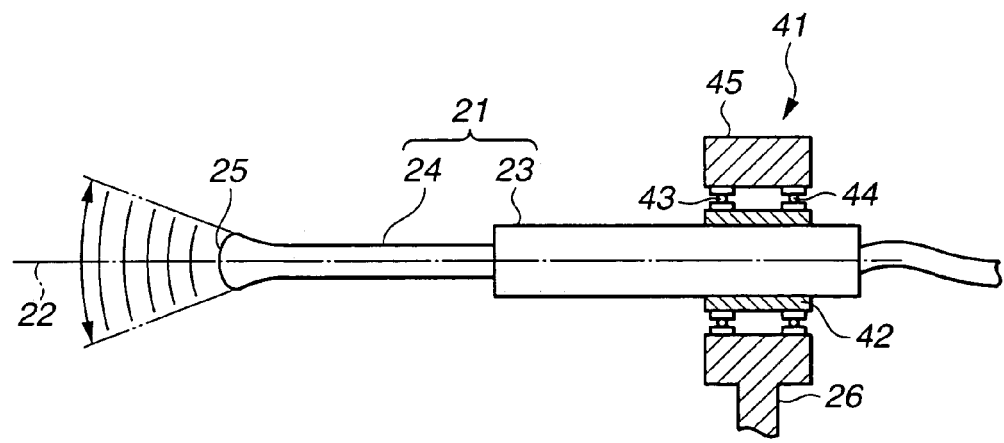
FIG. 15 is an explanatory diagram showing a state where an ultrasonic probe is fixed to a holding unit according to the fifth embodiment of the invention.
Figure 16:
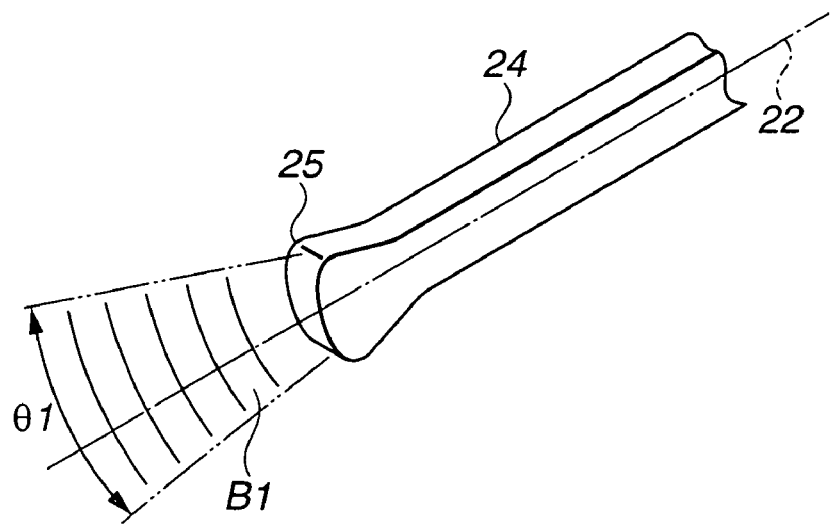
FIG. 16 is an explanatory diagram showing an image rendering plane of the ultrasonic probe according to the fifth embodiment of the invention.
Figure 17:
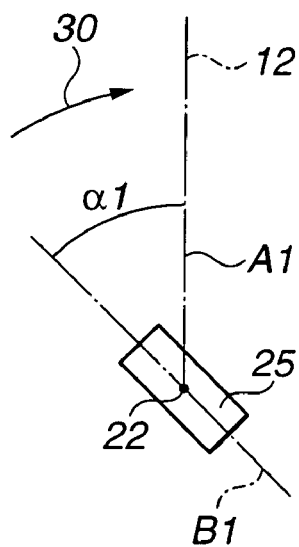
FIG. 17 is a concept diagram showing a relationship between an endoscope inserting axis and the image rendering plane of the ultrasonic probe according to the fifth embodiment of the invention.
Figure 18:
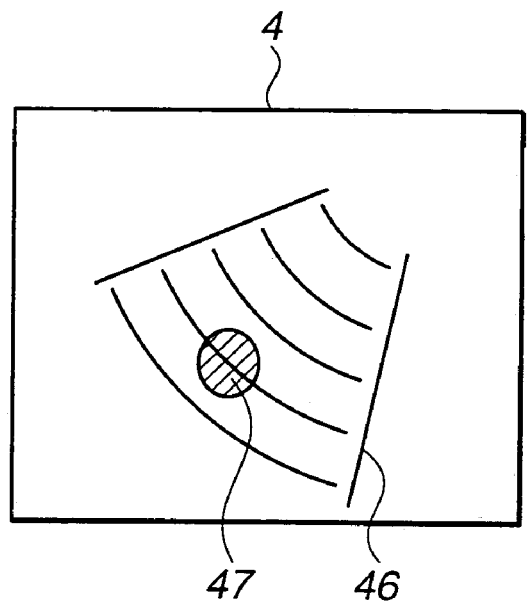
FIG. 18 is a first explanatory diagram of an ultrasonic image rendered by the ultrasonic probe according to the fifth embodiment of the invention.
Figure 19:
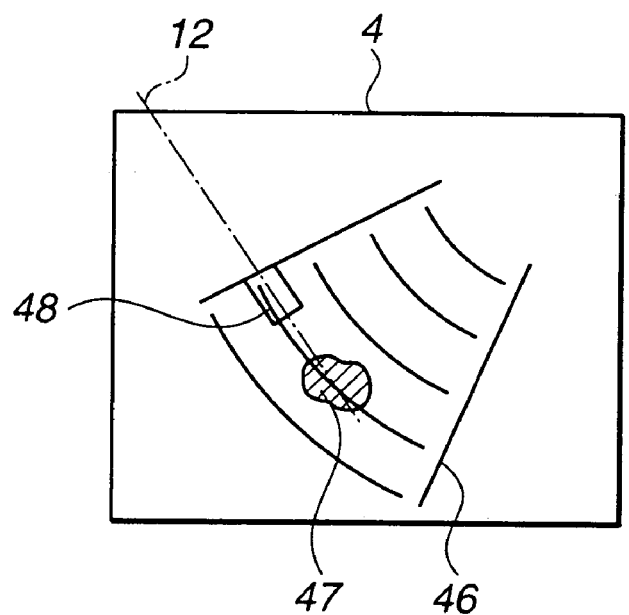
FIG. 19 is a second explanatory diagram of an ultrasonic image rendered by the ultrasonic probe according to the fifth embodiment of the invention.

FIGS. 14 to 19 relate to a fifth embodiment. FIG. 14 is an explanatory diagram showing an entire construction of an endoscope operation system. FIG. 15 is an explanatory diagram showing a state where an ultrasonic probe is fixed to a holding unit. FIG. 16 is an explanatory diagram showing an image-rendering plane of the ultrasonic probe. FIG. 17 is a concept diagram showing a relationship between an endoscope inserting axis and the image-rendering plane of the ultrasonic probe. FIG. 18 is a first explanatory diagram of an ultrasonic image rendered by the ultrasonic probe. FIG. 19 is a second explanatory diagram of an ultrasonic image rendered by the ultrasonic probe.

[Construction]

First of all, the entire construction of an endoscope operation system applying an ultrasonic observation system of the invention will be described with reference to FIG. 14.

As shown in. FIG. 14, an endoscope operation system 1 includes an endoscope 11, an ultrasonic probe 21, holding units 16 and 26, a three-dimensional position observation apparatus 31 and a position correcting unit 41.

The endoscope 11 is used to optically observe an object to be operated 3 of a patient 2.

The ultrasonic probe 21 is used to ultrasonically observe the object to be operated 3.

A navigation equipment includes the three-dimensional position observation apparatus 31, a sensor arm 32, which will be described below, and a workstation, not shown. The navigation equipment is included in a three-dimensional position determining means for determining a three-dimensional position of the endoscope 11 and the ultrasonic probe 21 with respect to the object to be operated 3.

The three-dimensional position observation apparatus 31, the sensor arm 32 and the workstation, not shown, can have the same constructions, which have been described in detail in the second and third embodiments. Therefore, the detail description will be omitted here.

The position correcting unit 41 holds the ultrasonic probe 21 rotatably around a center axis 22 of the ultrasonic probe 21. The position correcting unit 41 rotates a two-dimensional plane of an ultrasonic image (ultrasonic observation plane) rendered by the ultrasonic probe 21 around the center axis 22 of the ultrasonic probe 21 so that the plane including the center axis 12 of the endoscope 11 and the object to be operated 3 can substantially coincide with the ultrasonic observation plane by the ultrasonic probe 21.

The endoscope operation system 1 will be further described in detail below.

The endoscope 11 includes an inserting portion 13 having a small diameter, an eyepiece 14, and a TV camera 15.

An endoscopically observed image is guided to the eyepiece 14 by an objective lens at the distal end 19 of the inserting portion 13 and by an internal relay optical system, not shown, and is enlarged by the eyepiece 14.

The TV camera 15 is optically connected to the eyepiece 14 of the endoscope 11.

The TV camera 15 captures an endoscopically-observed image enlarged by the eyepiece 14, and the image is displayed by a TV camera driving unit and monitor, not shown, on the screen of the monitor as the endoscopically-observed image.

The holding unit 16 grasps and fixes the endoscope 11 three-dimensionally and freely. The holding unit 16 is mounted to a frame 17 on an operation bed, not shown, by using a connecting portion 18.

The ultrasonic probe 21 is of the front scanning type, which is the same as the type of the ultrasonic probe, which has been described in detail in the first to fourth embodiments. The ultrasonic probe 21 scans the front of a distal end 25 of an ultrasonically-observing portion 24, which is an inserting portion, and renders an ultrasonic image.

The ultrasonic probe 21 is grasped and is fixed by the position correcting unit 41 at one end of the holding unit 26. The other end of the holding unit 26 is mounted to a frame 27 on the operation bed, not shown, by using a connecting portion 28.

On the other hand, a sensor arm 32 included in the navigation equipment is mounted to the endoscope 11. The sensor arm 32 has three light-emitting diodes (called LED, hereinafter) 33 for emitting infrared light.

These LED's 33 are provided at predetermined positions with respect to the distal end 19 of the endoscope 11 (at positions apart from the distal end of the endoscope 11 by known distances) and with respect to a center axis 12. Thus, the axial direction of the endoscope 11 and the position of the distal end 19 can be detected by these three LED's 33.

The three-dimensional position observation apparatus 31 in the navigation equipment detects infrared rays from the three LED's 33 of the sensor arm 32 by using infrared ray receiving portions 34 and 35.

The three-dimensional observation apparatus 31, in combination with a workstation, not shown, measures the position and/or direction of the receiving sensor arm 32, that is, the distal end position and the center axis 12 of the endoscope 11, based on the infrared ray detection result. Then, the three-dimensional position observation apparatus 31 displays on the monitor the distal end position of the endoscope 11 with respect to the head of the patient. The detail technical matters relating to the navigation equipment has been described in the second and third embodiments, and the description will be therefore omitted here.

A sensor arm 36 is mounted to the ultrasonic probe 21. The sensor arm 36 has three LED's 37 for emitting infrared light.

These LED's 37 are provided at predetermined positions with respect to the distal end 25 of the ultrasonic probe 21 (at positions apart from the distal end of the ultrasonic probe 21 by known distances) and with respect to the center axis 22. Thus, the axial direction of the ultrasonic probe 21 and the position of the distal end 25 of the probe 21 can be detected by these three LED's 37.

Like the case of the endoscope 11, the three-dimensional position observation apparatus 31 detects infrared rays from the three LED's 37 of the sensor arm 36 by using the infrared ray receiving portions 34 and 35. Then, the three-dimensional position observation apparatus 31 measures the position and/or direction of the sensor arm 36, that is, the distal end position and center axis 22 of the ultrasonic probe 21 based on the infrared ray detection result.

In this embodiment, the connecting portions 18 and 28 are positioned and are fixed at the reference positions. Therefore, by using infrared rays from the respectively positioned LED's 33 and 37, the axial directions of the endoscope 11 and ultrasonic probe 21, the position of the distal end 19 of the endoscope 11 and the position of the distal end 25 of the ultrasonic probe 21 can be detected.

Next, the state of the connection between the ultrasonic probe 21 and the holding unit 26 will be described with reference to FIGS. 15 and 16.

As shown in FIG. 15, the ultrasonic probe 21 includes a holding portion 23 and an ultrasonic observing portion 24. The ultrasonic observing portion 24 incorporates an ultrasonic vibrator and an audio lens at the distal end 25 and can be inserted into a body cavity.

As shown in FIG. 16, an image rendering plane B1 ultrasonically observed by the ultrasonic observing portion 24 is two dimensional having an angle θ1. The direction is substantially the same as the longitudinal direction of the distal end 25.

As shown in FIG. 15, the holding portion 23 of the ultrasonic probe 21 is grasped and is fixed at one end of the holding unit 26 by the position correcting unit 41. In FIG. 15, the sensor arm 36 and the LED's 37 in the ultrasonic probe 21 are omitted.

The position correcting unit 41 includes a grasping portion 42, bearings 43 and 44 and an end 45 of the holding unit 26.

The grasping portion 42 can be integrally mounted to the holding portion 23.

The end 45 has a ring-shape, and the grasping portion 42 is mounted freely rotatably around the center axis 22 within the ring-shape through the bearings 43 and 44.

[Operation]

In the fifth embodiment, an operator operates the holding unit 16 by checking the position of the distal end 19 of the endoscope 11 by using the three-dimensional position observation apparatus 31 shown in FIG. 14 and moves the center axis 12 of the endoscope 11 toward the part to be operated 3. Similarly, the center axis 22 of the ultrasonic probe 21 is moved toward the part to be operated 3 by using the three-dimensional position observation apparatus 31. Then, the operator inserts the ultrasonically observing portion 24 of the ultrasonic probe 21 into the body cavity of the patient 2 along the center axis 22 until the image of the part to be operated 3 can be rendered. Thus, the image of the part to be operated 3 is rendered on the ultrasonic image on the monitor, for example.

Next, the operator inserts the endoscope 11 toward the part to be operated 3 along the center axis 12. Here, as shown in FIGS. 16 and 17, when the image rendering plane B1 of the ultrasonic probe 21 is displaced by an angle α1 from a plane A1 including the center axis 12 of the endoscope 11 and the center axis 22 of the ultrasonic probe 21, an image 47 of the part to be operated 3 is displayed but the distal end 19 of the endoscope 11 is not displayed on the ultrasonic image 46 on the screen of the monitor as shown in FIG. 18 unless the distal end 19 of the endoscope 11 intersects the image rendering plane B1 of the ultrasonic probe 21.

Therefore, the operator rotates the ultrasonic probe 21 together with the grasping portion 42 by the angle α1 in a direction indicated by an arrow 30 around the center axis 22 shown in FIG. 17 with respect to the holding unit 26 by using the bearings 43 and 44. Thus, when the distal end 19 of the endoscope 11 is positioned on the image rendering plane B1 of the ultrasonic probe 21 in the range (angle θ1) where ultrasonic transmitted from the ultrasonic probe 21 is scanned, the distal end 19 of the endoscope 11 is rendered as a bright point 48 on the ultrasonic image 46 as shown in FIG. 19. Therefore, the operator inserts the endoscope 11 to the part to be operated 3 by checking the ultrasonic image 46.

When the distal end 19 of the endoscope 11 is at the twisted position with respect to the two-dimensional image plane of the ultrasonic probe 21, the ultrasonic probe 21 is rotated gradually around the center axis 22 for matching.

[Advantages]

According to the fifth embodiment, the endoscope 11 and the ultrasonic probe 21 are held by the holding units 16 and 26, respectively, so that the degree of freedom can be obtained. Thus, the center axis 12 of the endoscope 11 and the center axis 22 of the ultrasonic probe 21 can be easily adjusted toward the part to be operated 3.

The three-dimensional state of an object to be observed in an operation space can be recognized. In other words, the ultrasonic probe 21 is mounted to the holding unit 26 through bearings 43 and 44. Thus, the displacement toward the center axis 22 of the ultrasonic probe 21 can be eliminated. Therefore, the ultrasonic probe 21 can be rotated easily around the center axis 22.

In this way, the distal end 19 can be displayed accurately on the ultrasonic image 46 by the ultrasonic probe 21. Thus, the movement of the distal end 19 of the endoscope 11 can be observed accurately, and the distal end 19 of the endoscope 11 can be guided accurately to the part to be operated. As a result, the work efficiency of operations can be improved.

In this embodiment, the construction has been described where the navigation of the ultrasonic probe 21 and the endoscope 11 is performed by using the three-dimensional position observation apparatus 31. However, the ultrasonic observation system may not have to include the three-dimensional position observation apparatus 31. In this case, by gradually rotating the ultrasonic probe 21 around the center axis 22 for the agreement, the distal end 19 of the endoscope 11 can be rendered on the ultrasonic image 46 as the bright point 48, as shown in FIG. 19.

Sixth Embodiment

Figure 20:
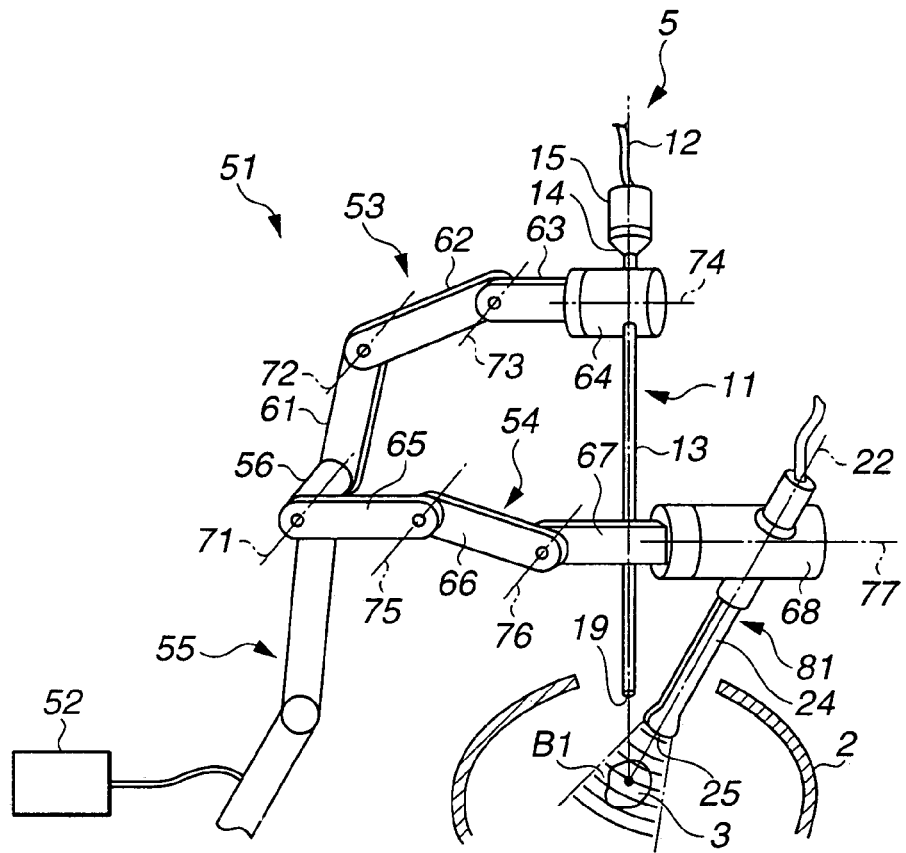
FIG. 20 is an explanatory diagram showing an entire construction of an endoscopic operation system according to a sixth embodiment of the invention.
Figure 21:
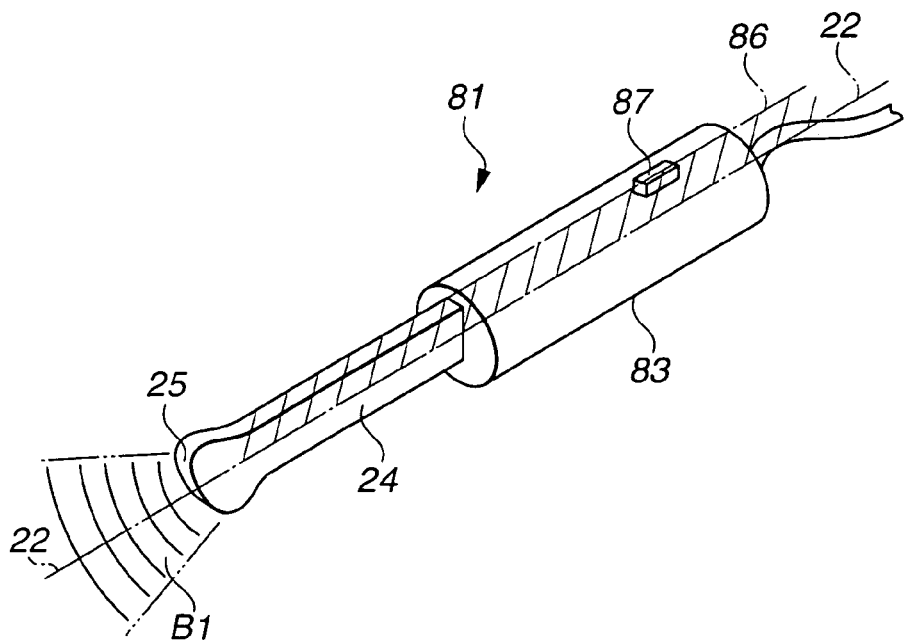
FIG. 21 is a perspective view of an ultrasonic probe according to the sixth embodiment of the invention.
Figure 22:
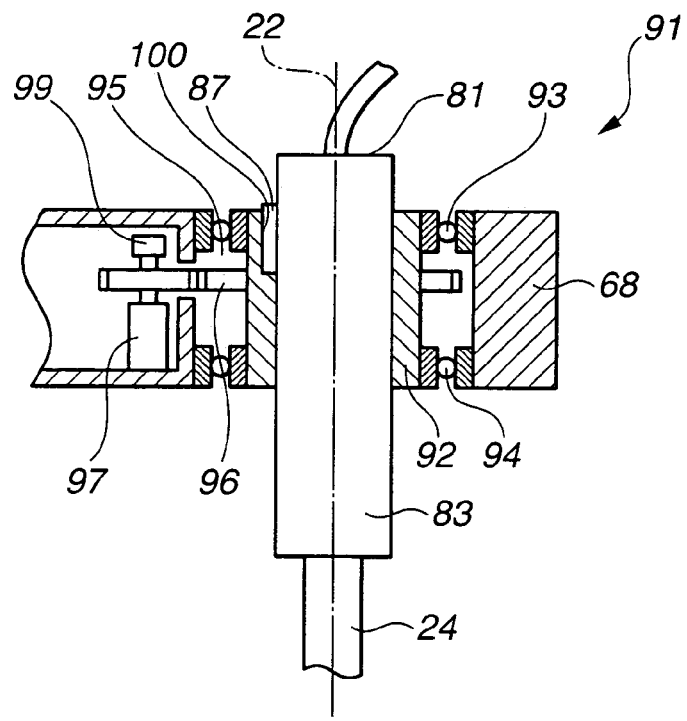
FIG. 22 is a sectional view showing a state where an ultrasonic probe is fixed to a holding unit according to the sixth embodiment of the invention.

FIGS. 20 to 22 relate to a sixth embodiment of the invention. FIG. 20 is an explanatory diagram showing an entire construction of an endoscope operation system according to this embodiment. FIG. 21 is a perspective view of an ultrasonic probe. FIG. 22 is a sectional view showing a state where an ultrasonic probe is fixed to a holding unit.

In FIGS. 20 to 22, the same reference numerals are given to the same component as those of the fifth embodiment, and the description will be omitted herein.

[Construction]

The entire construction of an endoscope operation system will be described first with reference to FIG. 20.

As shown in FIG. 20, an endoscope operation system 5 includes an endoscope 11, an ultrasonic probe 81, a holding unit 51 and a control portion 52.

The holding unit 51 is mounted to, for example, an operation bed, not shown, like the fifth embodiment and holds the endoscope 11 and the ultrasonic probe 81.

More specifically, the holding unit 51 includes an endoscope arm portion 53, an ultrasonic probe arm portion 54, and a supporting arm portion 55. The endoscope arm portion 53 is used to mount the endoscope 11. The ultrasonic probe arm portion 54 is used to mount the ultrasonic probe 81. The supporting arm portion 55 supports the endoscope arm portion 53 and the ultrasonic probe arm portion 54.

The supporting arm portion 55 is mounted to, for example, an operation bed at one end and has a mounting portion 56 for mounting the endoscope arm portion 53 and the ultrasonic probe arm portion 54 at the other end. The supporting arm portion 55 can adjust the position of the mounting portion 56 three-dimensionally.

The endoscope arm portion 53 includes arms 61, 62 and 63. The arms 61, 62 and 63 can rotate around rotational axes 71, 72 and 73, respectively. Encoders for detecting the rotational angles of the arms are mounted on the rotational axes 71, 72 and 73 of the arms 61, 62 and 63.

One end of an endoscope holding portion 64 is mounted to the arm 63 rotatably around an axis 74. The endoscope 11 is mounted integrally to the other end of the endoscope holding portion 64. An encoder for detecting the rotational angle of the endoscope holding portion 64 with respect to the arm 63 is mounted on the rotational axis 74.

The ultrasonic probe arm portion 54 includes arms 65, 66 and 67. The arms 65, 66 and 67 can rotate around rotational axes 71, 75 and 76. Encoders for detecting the rotational angles of the arms are mounted to the rotational axes.

One end of an ultrasonic probe holding portion 68 is mounted rotatably to the arm 67 around an axis 77. The ultrasonic probe 81 is mounted integrally to the other end of the ultrasonic probe holding portion 68. An encoder for detecting the rotational angle of the ultrasonic probe 81 with respect to the arm 67 is mounted on the rotational axis 77 of the ultrasonic probe holding portion 68.

The control portion 52 is electrically connected to the encoders mounted to the rotational axes 71, 72, 73, 74, 75, 76 and 77 of the holding unit 51.

The control portion 52 includes a computing circuit for calculating the three-dimensional positions and directions of the endoscope holding portion 64 and the ultrasonic probe holding portion 68 based on the output values of the encoders. With this construction, in this embodiment, a three-dimensional position determining means is provided in the holding unit 51. The three-dimensional position determining means determines the three-dimensional positions (the encoders) of the endoscope 11 and the ultrasonic probe 81 with respect to the part to be operated 3.

As shown in FIG. 21, a positioning portion 87 (a projection and/or a depression) is provided in the grasping portion 83 of the ultrasonic probe 81. The positioning portion 87 is used to position the center axis 86 within the image rendering plane B1 of the ultrasonic probe 81. In this case, the plane formed by connecting the center line of the positioning portion 87 and the center axis 86 is preferably the same as the image rendering plane B1.

The construction for mounting the ultrasonic probe 81 to the ultrasonic probe holding portion 68 will be described with reference to FIG. 22.

As shown in FIG. 22, an engaging portion (fitting portion) 100 for engaging with or fitting to the positioning portion 87 is provided on a fixing portion 92.

The engaging portion (fitting portion) 100 engages with or fits to the positioning portion 87 and integrally fixes the ultrasonic probe 81. The positioning portion 87 is provided apart from the distal end 25 of the ultrasonic probe 81 by a known distance. Therefore, the positioning portion 87 engages with or fits to the fixing portion 92 and is fixed rotatably to the ultrasonic probe holding portion 68. That is, the distal end 25 of the ultrasonic probe 81 is fixed apart from the ultrasonic probe holding portion 68 by a predetermined distance.

The ultrasonic probe holding portion 68 has an opening 95, and the fixing portion 92 is freely rotatably mounted around the center axis 22 through bearings 93 and 94 within the opening 95.

A gear 96 is integrally mounted to the periphery of the fixing portion 92. A motor 97 is fixed within the ultrasonic probe holding portion 68. A gear 98 is mounted to an output axis of the motor 97 so as to engage with the gear 96. An encoder 99 is mounted on an output axis of the motor 97.

Calibration is set between the encoder 99 and the rotating position of the engaging portion (fitting portion) 100 at the initial setting during the assembly. Therefore, when the positioning portion 87 engages with or fits to the engaging portion (fitting portion) 100, the scanning direction of the ultrasonic transmitted from the distal end 25 of the ultrasonic probe 81 can be always recognized based on the output of the encoder 99.

A position correcting unit 91 according to the sixth embodiment includes the positioning portion 87, the fixing portion 92, the bearings 93 and 94, the gear 96, the motor 97, the gear 98 and the encoder 99.

With this construction, the position correcting unit 91 includes a rotating mechanism for rotating the ultrasonic probe 81 around the axis in accordance with the detection result from the detecting unit including the encoder. The rotating mechanism automatically operates into the set position determined in accordance with detection result from the detecting unit using the encoder.

[Operation]

According to the sixth embodiment, an operator rotates the arms 65, 66 and 67 of the holding unit 51 and the ultrasonic probe holding portion 68 around the rotational axes 71, 75, 76 and 77,i respectively, and moves the direction of the center axis 22 of the ultrasonic probe 81 toward a part to be operated 3.

Here, like the fifth embodiment, an image of the part to be operated 3 is rendered on the ultrasonic image.

Next, the arms 61, 62 and 63 of the holding unit 51 and the endoscope holding portion 64 are rotated around the rotational axes 71, 72, 73 and 74, respectively, and the center axis 12 of the endoscope 11 is moved to the position of the center axis 22 of the ultrasonic probe 81, which forms an image rendering plane B1 near the part to be operated 3.

Here, the operator turns on an input switch, not shown, so that the control portion 52 of the holding unit 51 can calculate the three-dimensional position of the center axis 12 of the endoscope 11 based on the output values (rotational angles) from the encoders incorporated in the rotational axes 71, 72, 73 and 74. Then, the three-dimensional position of the center axis 22 of the ultrasonic probe 81 is calculated based on the output values (rotational angles) from the encoders incorporated in the rotational axes 71, 75, 76 and 77.

Furthermore, the rotational angle with respect to the center axis 86 of the positioning portion 87 of the ultrasonic probe 81, that is, the rotational angle of the image rendering plane B1 with respect to the center axis 22 of the ultrasonic probe 81 is calculated from the output value from the encoder 99.

Here, as shown in FIG. 17 according to the fifth embodiment, when the image rendering plane B1 is displaced from the plane A1 including the center axis 12 of the endoscope 11 and the center axis 22 of the ultrasonic probe 81 (ultrasonic probe 21 in FIG. 17) by a displaced angle α1, the motor 97 is driven by a motor driving power supply and driving circuit, not shown.

The gear 98 is rotated by the driving of the motor 97. Thus, the gear 96 is rotated. That is, the ultrasonic probe 81 is rotated around the center axis 22. Here, the control portion 52 of the holding unit 51 terminates the driving of the motor 97 when the displaced angle α1 is zero (0) in accordance with the detection result from the encoder 99 for the rotational angle of the gear 98.

Here, when the distal end 19 of the endoscope 11 is positioned on the image rendering plane B1 of the ultrasonic probe 81 in the range (angle θ1) for scanning ultrasonic transmitted from the ultrasonic probe 81, the distal end of the endoscope 11 is displayed on the ultrasonic image as a bright point. On the other hand, when the center of the part to be operated 3 does not exist on the plane including the center axis 12 of the endoscope 11 and the center axis 22 of the ultrasonic probe 81, the image of the part to be operated 3 is rendered in a smaller range than that of the ultrasonic image before the motor 97 is driven.

Therefore, the operator manipulates the holding unit 51 again to slightly adjust the positions of the ultrasonic probe 81 and the endoscope 11, and the above-described operation is repeated again. Thus, the image rendering plane B1 by the ultrasonic probe 81, the center axis 12 of the endoscope 11 and the center of the part to be operated 3 are positioned on the same plane. Under this condition, the operator inserts the endoscope 11 to the part to be operated 3 by checking the ultrasonic image.

[Advantages]

According to the sixth embodiment, a three-dimensional state of the part to be observed in an operation space can be recognized. In other words, the direction of the image rendering plane B1 by the ultrasonic probe 81 is automatically adjusted in accordance with the three-dimensional position information of the ultrasonic probe 81 and the endoscope 11. Therefore, the center axis 12 of the endoscope 11 can be included on the image rendering plane B1 by the ultrasonic probe 81 easily.

Furthermore, since a large three-dimensional position observation apparatus is not required like the fifth embodiment, the complication of an operating room can be prevented.

In this embodiment, the endoscope 11 and the ultrasonic probe 81 are held by the single holding unit 51. However, as shown in FIG. 14, the endoscope 11 and the ultrasonic probe 81 may be held by separate holding units, respectively, and the reference of the holding units may be set (calibrated) initially.

In other words, each holding unit is positioned to the reference position, and the initial setting can be performed by detecting three-dimensionally and identifying the positions of the distal ends of the endoscope 11 and the ultrasonic probe 81 at the reference position and by recording the detection results in a recording medium such as a memory, not shown. Therefore, the same effects can be obtained as those of the sixth embodiment.

Furthermore, in this embodiment, the center axes of the endoscope 11 and ultrasonic probe 81 can be matched automatically. The construction example is shown in FIG. 33.

Figure 33:
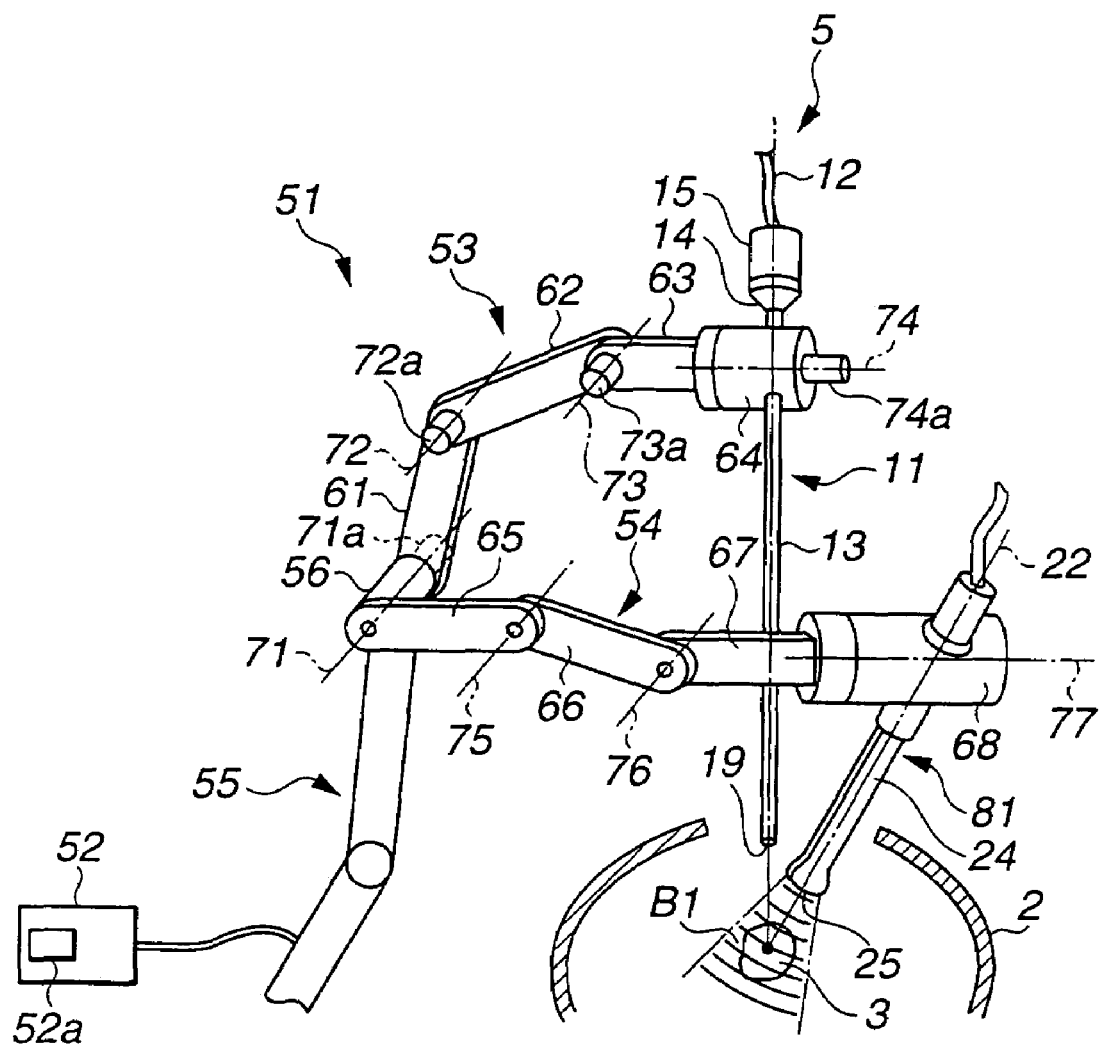
FIG. 33 is an explanatory diagram showing a variation example of the sixth embodiment of the invention and showing an entire configuration of the endoscope operation system.

As shown in FIG. 33, in the ultrasonic observation system of the example, motors 71a, 72a, 73a and 74a, which are driving units, are assembled respectively to the joints (more specifically near the rotational axes 71, 72 and 73 of the arms 61, 62 and 63 and near the axis 74 of the endoscope holding portion 64), of the endoscope arm portion 53 of the endoscope 11.

The motor 71a is provided near the rotational axis 71 of the arm 61 and drives to rotate the arm 61 around the rotational axis 71. The motor 72a is provided near the rotational axis 72 of the arm 62 and drives to rotate the arm 62 around the rotational axis 72. The motor 73a is provided near the rotational axis 73 of the arm 63 and drives to rotate the arm 63 around the rotational axis 73. The motor 74a is provided on the axis 74 of the endoscope holding portion 64 and drives to rotate the endoscope holding portion 64 around the axis 74.

The motors 71a, 72a, 73a and 74a are electrically connected to the control portion 52 and the driving of the motors is controlled by the control portion 52.

In the ultrasonic observation system having the construction, when the center axis of the endoscope 11 is at the twisted position with respect to the image rendering plane B1 of the ultrasonic probe 81, for example, the control portion 52 controls the driving of the motors 71a, 72a, 73a and 74a such that the center axis 22 of the ultrasonic probe 81 intersects the center axis of the endoscope 11. Thus, the arms 61, 62 and 63 and the endoscope holding portion 64 are rotated.

In this way, the drive control by the control portion 52 matches the center axis of the endoscope 11 and the center axis 22 of the ultrasonic probe 81. In this case, the endoscope 11 is moved to the outside of the head in advance and then is inserted to the part to be operated 3 toward the center axis.

Thus, the matching operation of the center axis 22 of the ultrasonic probe 81 and the center axis of the endoscope 11 according to the sixth embodiment can be performed automatically with the simple construction at low costs, which greatly contributes to the improvement of the work efficiency in operations.

In this example, the control portion 52 further includes a display portion 52a having an LED, a buzzer, and/or the like. When the center axis of the endoscope 11 and the center axis 22 of the ultrasonic probe 81 coincide each other as described above, the control portion 52 can light up the LED of the display portion 52a or can control the buzzer to sound concurrently with the LED lighting-up. Thus, the state where the center axis of the endoscope 11 and the center axis 22 of the ultrasonic probe 81 coincide can be informed to the operator instantly with the simple construction.

The display portion 52a may display text information in addition to the LED display and the buzzer sounding to inform the state to the operator.

Seventh Embodiment

Figure 23:
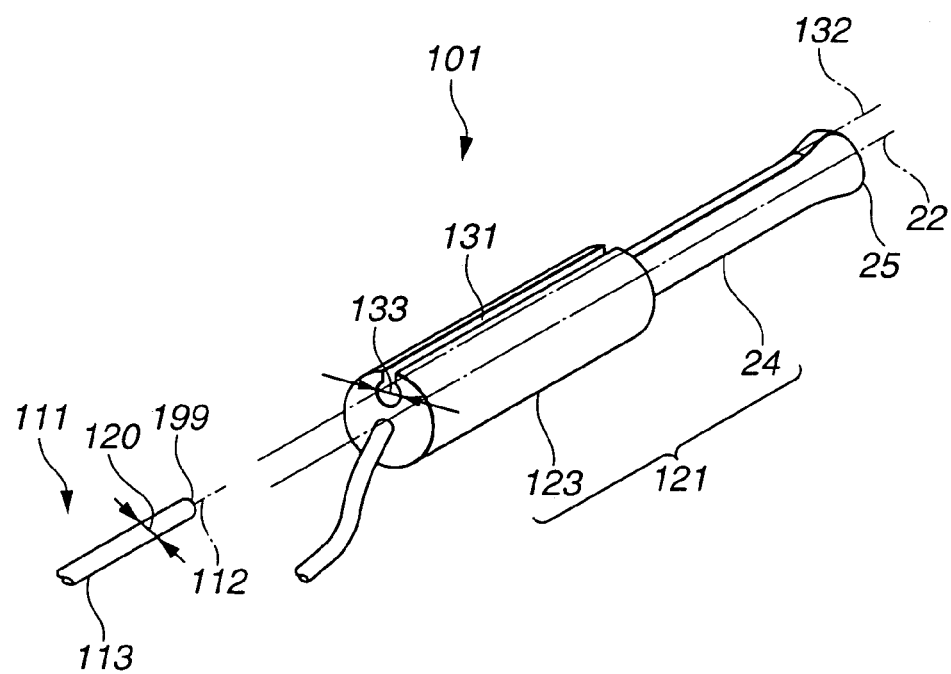
FIG. 23 is a perspective view of an ultrasonic probe according to a seventh embodiment of the invention.

FIGS. 23 to 25 relate to a seventh embodiment. FIG. 23 is a perspective view of an ultrasonic probe. FIG. 24 is a partial cut-out sectional view showing the ultrasonic probe. FIG. 25 is an explanatory diagram of an ultrasonic image rendered by the ultrasonic probe.

In the description with reference FIGS. 23 to 25, the same reference numerals are given to the same components as those of the fifth and sixth embodiments, and the description will be omitted herein.

[Construction]

As shown in FIGS. 23 and 24, an endoscope operation system 101 includes an endoscope 111 and an ultrasonic probe 121.

The ultrasonic probe 121 includes a holding portion 123 and an ultrasonically observing portion 24.

A grasping portion 123 of the ultrasonic probe 121 has an endoscope inserting hole 131. A center axis 132 of the endoscope inserting hole 131 is substantially parallel with the center axis 22 of the ultrasonic probe 121 and on the same plane as an ultrasonically observed image rendering plane B1. An internal diameter 133 of the endoscope inserting hole 131 and an external diameter 120 of the inserting portion 113 of the endoscope 111 fit into each other such that the center axes 112 and 132 can substantially match.

With this construction, the endoscope inserting hole 131 can be a guiding means for guiding the distal end position of the endoscope 111 into the ultrasonically observable range observed by the ultrasonic probe 121.

In FIGS. 23 and 24, the endoscope inserting hole 131 is a so-called partial cut-out open to the grasping portion 123 but may be a complete hole. The ultrasonic probe 121 may be held by hand or may be held by the holding unit 26 according to the fifth embodiment.

[Operation]

As shown in FIG. 24, an operator inserts the ultrasonic probe 121 to a part to be operated 3 in order to check the position of the part to be operated 3. Here, like the fifth and sixth embodiments, an image 47 of the part to be operated 3 is rendered on an ultrasonic image 46 shown in FIG. 25.

Next, by checking the position of the part to be operated 3 on the ultrasonic image 46, the operator inserts the inserting portion 113 of the endoscope 111 to the endoscope inserting hole 131 of the ultrasonic probe 121. The inserting portion 113 is inserted toward the part to be operated 3 along the center axis 132. When the distal end 119 reaches the image rendering plane B1 to be ultrasonically observed, the distal end 119 is rendered on the ultrasonic image 46 as a bright point 148 as shown in FIG. 25.

After that, the operator leads the endoscope 11 to the part to be operated 3 by checking the part to be operated 3 and the distal end 19 of the endoscope 11 on the ultrasonic image 46.

[Advantages]

According to the seventh embodiment, with the simple construction where the grasping portion 123 of the ultrasonic probe 121 has the endoscope inserting hole 131 in which the center axis is positioned on the same plane as the image rendering plane B1, the endoscope 111 can be guided to the part to be operated 3 accurately. Furthermore, since the endoscope 111 is inserted from the ultrasonically observed direction, the orientation with respect to the part to be operated 3 can be easily adjusted.

Eighth Embodiment

Figure 26:
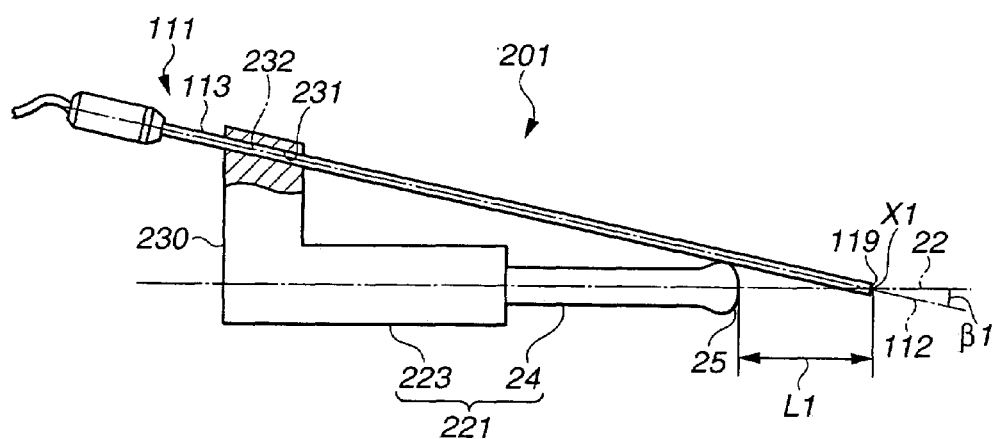
FIG. 26 is a partial cut-out sectional view of an endoscope and ultrasonic probe according to an eighth embodiment of the invention.

FIG. 26 is a partial cut-out sectional view of an endoscope and ultrasonic probe according to an eighth embodiment of the invention.

In the description with reference to FIG. 26, the same reference numerals are given to the same components as those of the fifth to seventh embodiments, and the description will be omitted here.

[Construction]

As shown in FIG. 26, an endoscope operation system 201 includes an endoscope 111 and an ultrasonic probe 221.

The ultrasonic probe 221 includes a holding portion 223 and an ultrasonically-observing portion 24.

A projection 230 projecting toward the external diameter is provided on the proximal end of the grasping portion 223 of the ultrasonic probe 221. The projection 230 has an endoscope inserting hole 231 to which an inserting portion 113 of the endoscope 111 fits.

The center axis 232 of the endoscope inserting hole 231 and the center axis 112 of the endoscope 111 have a predetermined angle $\beta1$ from the center axis 22 of the ultrasonically-observing portion 24 in the same plane as the image rendering plane B1 (see FIG. 24) of the ultrasonic image. The intersecting point X1 of the center axis 112 and the center axis 22 is positioned at the location apart from the distal end 25 by a distance L1, which is a distance (that is, the reachable range) that the ultrasonic probe 221 can render an image surely.

With this construction, the endoscope inserting hole 231 can be a guiding unit for guiding the distal end position of the endoscope 111 to the point X1 on the substantially center axis 22 of the ultrasonic probe 221 in the ultrasonically observable range observed by the ultrasonic probe 221.

[Operation]

According to the eighth embodiment, like the seventh embodiment, an operator inserts the ultrasonic probe 221 toward a part to be operated 3 (see FIG. 24) and checks the position of the part to be operated 3 on the ultrasonic image.

Next, by checking the position of the part to be operated 3 on the ultrasonic image, the inserting portion 113 of the endoscope 11 is inserted to the endoscope inserting hole 231 of the ultrasonic probe 221. Thus, the inserting portion 113 is inserted toward the part to be operated 3 along the center axis 112. When the distal end 119 reaches the image rendering plane B1 (see FIG. 24) to be ultrasonically observed, the distal end 119 is rendered as a bright point on the ultrasonic image like the seventh embodiment.

Next, the operator further inserts the endoscope 111. slowly by slightly adjusting the position of the ultrasonic probe 221 such that the center of the part to be operated 3 can substantially match with the intersecting point X1 of the center axes 22 and 112 of the ultrasonic probe 221 and endoscope 11. Thus, the distal end of the endoscope 111 is guided to the center of the part to be operated 3 securely.

[Advantages]

According to the eighth embodiment, the center axis 22 of the ultrasonic probe 221 and the center axis 112 of the endoscope 111 intersect at the penetrating range L1. Therefore, the distal end 119 of the endoscope 111 can be guided to the center of the ultrasonically observed range of the part to be operated 3 easily and securely.

Ninth Embodiment

Figure 27:
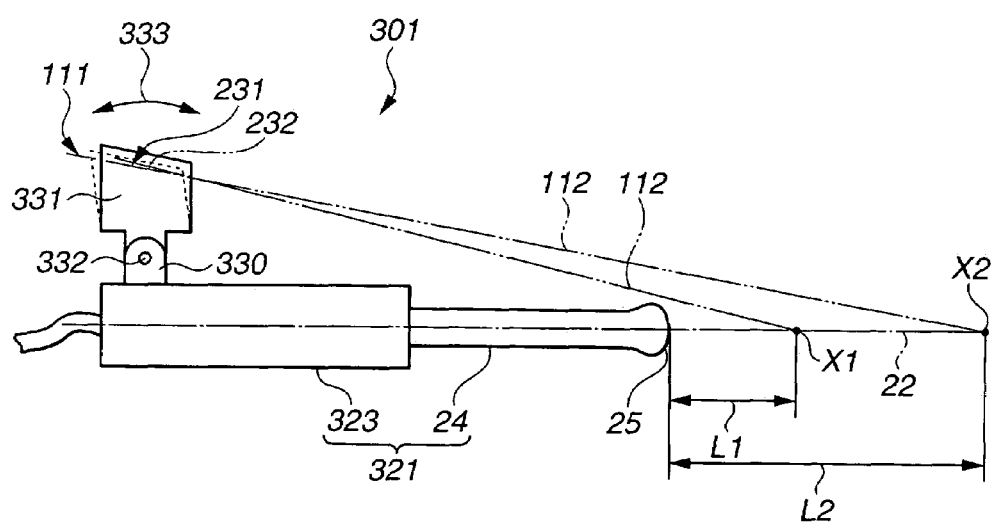
FIG. 27 is a partial cut-out sectional view of an endoscope and ultrasonic probe according to a ninth embodiment of the invention.

FIG. 27 is a partial cut-out sectional view of an endoscope and ultrasonic probe according to a ninth embodiment of the invention.

In the description with reference to FIG. 27, the same reference numerals are given to the same components as those of the fifth to eighth embodiments, and the description will be omitted here.

[Construction]

As shown in FIG. 27, an ultrasonic probe 321 of an endoscope operation system 301 includes a holding portion 323 and an ultrasonically-observing portion 24.

A mounting base 330 projecting toward the external diameter is provided on the proximal end of the grasping portion 323 of the ultrasonic probe 321. An endoscope holding portion 331 is mounted to the mounting base 330 rotatably in a direction indicated by an arrow 333 around an axis 332.

The endoscope holding portion 331 includes an endoscope inserting hole 231 to which the inserting portion 113 of the endoscope 111 shown in FIG. 26 fits.

The intersecting portion X1 of the center axis 112 of the endoscope 111 and the center axis 22 of the ultrasonic probe 321 is moved to a destination point X2 by the rotation of the endoscope holding portion 331 in the direction indicated by the arrow 333. The distance L2 from the distal end 25 of the ultrasonic probe 321 to the destination point X2 is in the reachable range of the ultrasonic probe 321.

With this construction, the mounting base 330, the endoscope holding portion 331 and the axis 332 can be included in a changing mechanism for changing the position of the intersecting point on the center axis 22.

[Operation]

According to the ninth embodiment, like the eighth embodiment, an operator inserts the ultrasonic probe 321 toward the part to be operated 3 shown in FIG. 24 and checks the position of the part to be operated 3 on the ultrasonic image.

Next, by checking the position of the part to be operated 3 on the ultrasonic image, the operator inserts the inserting portion 113 of the endoscope 11 into the endoscope inserting hole 231 of the ultrasonic probe 321. The inserting portion 113 is inserted toward the part to be operated 3 along the center axis 132 shown in FIG. 24. When the distal end reaches the image rendering plane B1 to be ultrasonically observed, the distal end is rendered as a bright point on the ultrasonic image shown in FIG. 25 like the eighth embodiment.

Next, the operator further inserts the endoscope 111 slowly by rotating the endoscope holding portion 331 in the direction indicated by the arrow 333 in the range from the intersecting point X1 to the intersecting point X2. Thus, the distal end of the endoscope 111 is guided to the center of the part to be operated 3 securely.

[Advantages]

According to the ninth embodiment, the position of the intersecting point of the center axis 22 of the ultrasonic probe 321 and the center axis 112 of the endoscope 111 can be adjusted. Therefore, an operator can move the distal end of the endoscope 111 to the center of the ultrasonically observed range of the part to be operated 3 without moving the position of the ultrasonic probe 321. Therefore, the endoscope 111 can be guided to the part to be operated 3 more easily.

Tenth Embodiment

Figure 28:
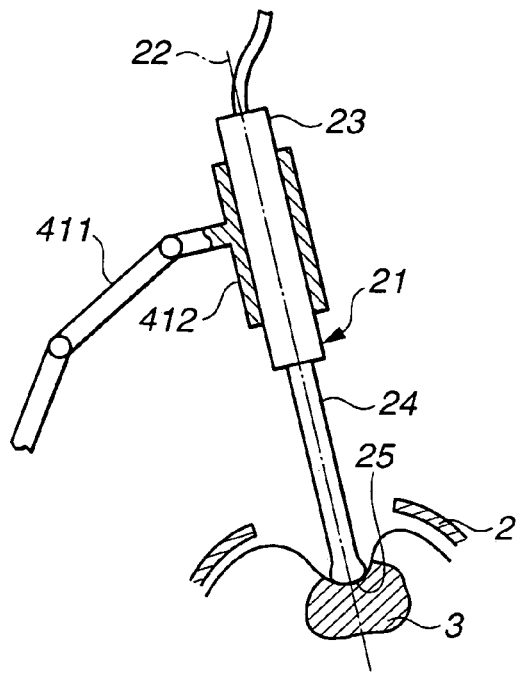
FIG. 28 is an explanatory diagram showing a state where an ultrasonic probe is guided to a part to be operated according to a tenth embodiment of the invention.
Figure 29:
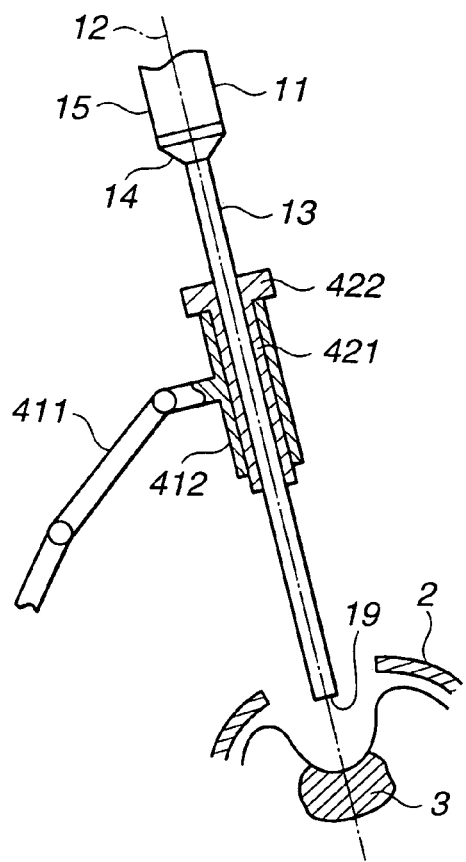
FIG. 29 is an explanatory diagram showing a state where an endoscope is guided to a part to be operated according to the tenth embodiment of the invention.
Figure 30:
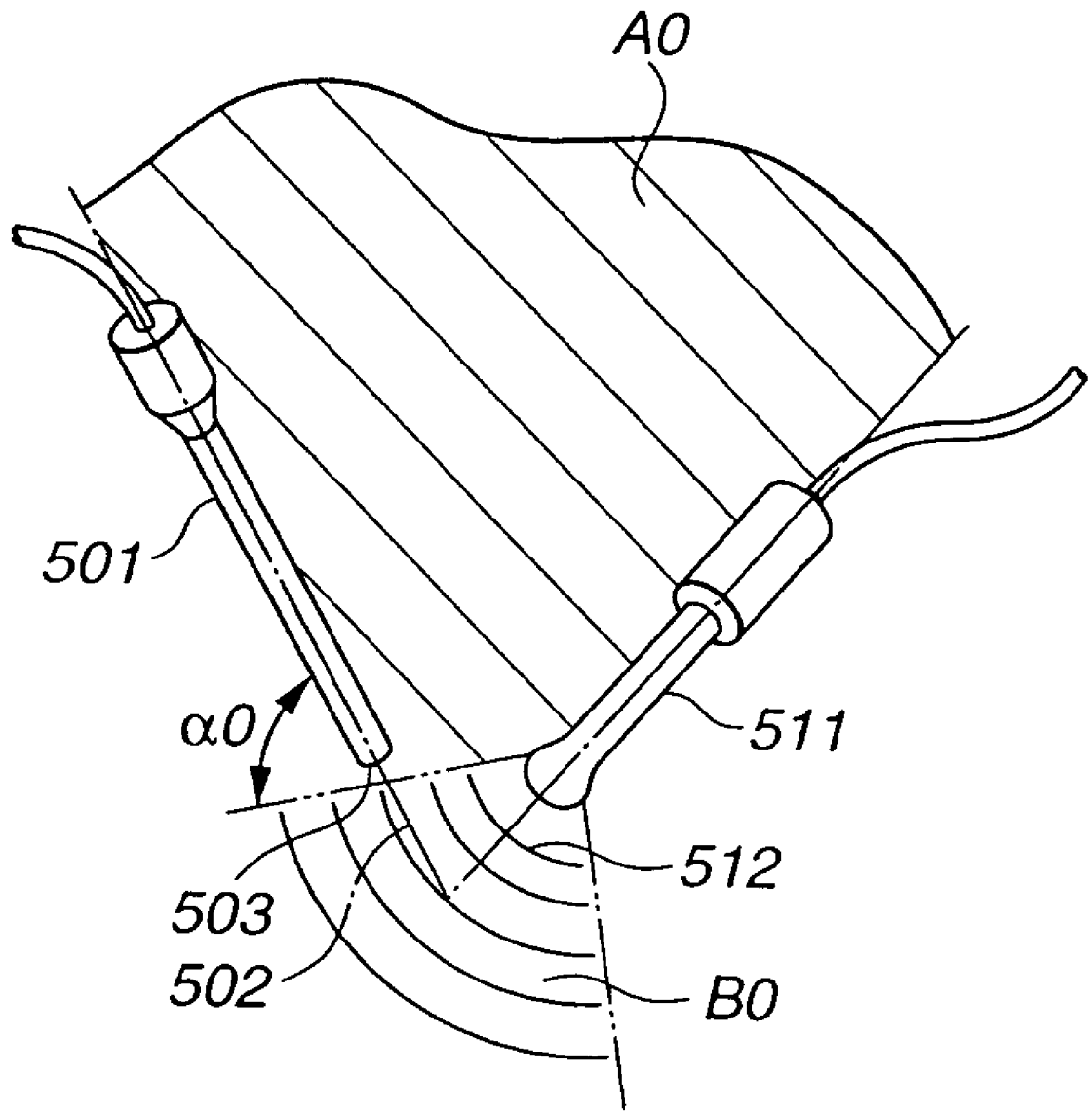
FIG. 30 is an explanatory diagram showing a problem due to positions of a conventional endoscope and ultrasonic probe.

FIGS. 28 and 29 relate to a tenth embodiment of the invention. FIGS. 28 and 29 are explanatory diagrams where an ultrasonic probe and an endoscope, respectively, are guided to the part to be operated 3.

In the description with reference to FIGS. 28 and 29, the same reference numerals are given to the same components as those of the fifth to ninth embodiments, and the description will be omitted here.

[Construction]

As shown in FIG. 28, an ultrasonic probe holding portion 412 is mounted at the distal end of a holding unit 411, and the ultrasonic probe 21 is held and is fixed at a three-dimensionally free position. A holding portion 23 can be inserted to the ultrasonic probe holding portion 412 such that the ultrasonic probe 21 can be retractably inserted in the direction of the center axis 22.

As shown in FIG. 29, an endoscope adapter 421 is a guiding unit according to this embodiment. The inserting portion 13 of the endoscope 11 can be inserted into the internal diameter coaxially.

The external diameter of the endoscope adapter 421 can be inserted to the ultrasonic probe holding portion 412 coaxially. A flange 422 is provided at the proximal end of the endoscope adapter 421. By adjusting the amount of projection of the distal end 19 of the endoscope 11 with respect to the flange 422, desired endoscope observation can be implemented.

With this construction, the endoscope adapter 421 can be a guiding unit for guiding the distal end position of the endoscope 11 to the point on the substantially center axis of the ultrasonic probe 21 in the ultrasonically observed range observed by the ultrasonic probe 21. The guiding unit is provided in the ultrasonic probe holding portion 412 of the holding unit. The guiding unit can be attached to the holding unit freely removably.

[Operation]

According to the tenth embodiment, an operator inserts the ultrasonic probe 21 to the ultrasonic probe holding portion 412 of the holding unit 411 first as shown in FIG. 28. Furthermore, the operator moves the holding unit 411 three-dimensionally and,causes the distal end 25 of the ultrasonic probe 21 to approach the part to be operated 3. Then, the distal end 25 of the ultrasonic probe 21 is rotated around the center axis 12 of the endoscope 11 with respect to the ultrasonic probe holding portion 412, and a desired ultrasonic image can be obtained. Thus, the position and/or depth of the part to be operated 3 can be checked.

Next, the ultrasonic probe 21 is removed from the ultrasonic probe holding portion 412 and the endoscope adapter 421 is inserted instead. Here, the center axis of the internal diameter of the endoscope adapter 421 is kept coaxial to the center axis 22 of the ultrasonic probe 21. Then, the inserting portion 13 of the endoscope 11 is inserted to the endoscope adapter 421. In other words, the center axis 12 of the endoscope 11 and the center axis 22 of the ultrasonic probe 21 are completely coaxial. Then, the operator moves the endoscope 11 straight along the center, axis 12. Thus, the distal end 19 of the endoscope 11 can be guided to the part to be operated 3.

[Advantages]

According to the tenth embodiment, the center axis 22 of the ultrasonic probe 21 and the center axis 12 of the endoscope 11 can be completely coaxial. Therefore, the distal end 19 of the endoscope 11 can be guided to the part to be operated 3 safely and securely. Furthermore, this embodiment can be implemented only by adding a simple construction, that is, an endoscope adapter, to the conventional holding unit. Therefore, this general-purpose embodiment costs significantly low and is used for the conventional holding units too.

The invention is not limited to the first to tenth embodiments and the change examples, and the combinations and applications of these embodiments and change examples can be applied to the invention.

In this invention, it is apparent that various modifications different in a wide range can be made on this basis of this invention without departing from the spirit and scope of the invention. This invention is not restricted by any specific embodiment except being limited by the appended claims.

What is claimed is:

1. An ultrasonic observation system, comprising:
   a long ultrasonic probe having an ultrasonic sending and receiving portion, which can send and receive ultrasound;
   a holder for holding the ultrasonic probe;
   a moving member connected to the holder such that the ultrasonic probe can move three-dimensionally;
   a signal generating member provided at a predetermined position of the ultrasonic probe;
   a detector for detecting a signal generated by the signal generating member, the detector detecting position information indicative of a three-dimensional direction of a center axis of the ultrasonic probe based on the generated signal;
   a regulator for regulating the movement of the moving member in order to prevent the ultrasonic sending and receiving portion from moving in the direction of the center axis;
   a rotation operating portion, which can rotate the ultrasonic probe around an axis, which is an arbitrary one direction of a plurality of propagation directions of the ultrasound transmitted from the ultrasonic sending and receiving portion;
   a memory for storing two-dimensional ultrasonically observed images of an object in a plurality of directions, which are obtained by the ultrasonic probe in accordance with the rotation operation by the rotation operating portion; and
   a three-dimensional image forming circuit for processing the position information detected by the detector and the two-dimensional ultrasonically-observed images from the memory so as to form a three-dimensional image.

2. The ultrasonic observation system according to claim 1, further comprising: a monitor; and an image processor for processing for displaying on the monitor an ultrasonically observed image of an object, which is obtained by the ultrasonic probe in accordance with the rotation operation by the rotation operation portion.

3. The ultrasonic observation system according to claim 2, wherein the image processor has a memory for storing position information and two-dimensional ultrasonically-observed image of an object, which is obtained by the ultrasonic probe in accordance with the rotation operation by the rotation operating portion; and a three-dimensional image forming circuit for processing on the position information and two-dimensional ultrasonically-observed image from the memory to form a three-dimensional image.

4. The ultrasonic observation system according to claim 1, wherein the regulator is a brake for regulating the movement of the moving member.

5. An ultrasonic observation system, comprising:
   a long ultrasonic probe having an ultrasonic sending and receiving portion, which can send and receive ultrasound, the ultrasound being oscillated at an arbitrary direction of oscillation directions from a center axis of the ultrasonic sending and receiving portion;
   a holder for holding the ultrasonic probe rotatably around the center axis;
   a moving member connected to the holder such that the ultrasonic probe can move three-dimensionally;
   a detector for detecting ultrasound oscillated by the ultrasonic sending and receiving portion, the detector detecting position information indicative of a three-dimensional direction from the center axis of the ultrasonic nrobe based on the oscillated ultrasound;
   a regulator for regulating the movement of the moving member in order to prevent the ultrasonic sending and receiving portion from moving in the direction of the center axis;
   an image processor for processing to form an ultrasonic image based on a first signal obtained by the ultrasonic sending and receiving portion;
   a monitor for displaying the ultrasonic image based on a second signal from the image processor;
   a memory for storing two-dimensional ultrasonically observed images of an object in a plurality of directions, which are obtained by the ultrasonic probe in accordance with the rotation operation by the rotation operating portion; and a three-dimensional image forming circuit for processing the position information detected by the detector and the two-dimensional ultrasonically-observed images from the memory so as to form a three-dimensional image.

6. The ultrasonic observation system according to claim 1, wherein the position information indicative of a three-dimensional direction relates to the rotation around the longitudinal axis of the ultrasonic probe.

7. The ultrasonic observation system according to claim 5, wherein the position information indicative of a three-dimensional direction relates to the rotation around the longitudinal axis of the ultrasonic probe.

* * * * *